United States Patent [19]
Butler et al.

[11] Patent Number: 5,409,958
[45] Date of Patent: Apr. 25, 1995

[54] USE OF ALKYL CYCLOPENTANONE AND PHENYL ALKANOL DERIVATIVE-CONTAINING COMPOSITIONS FOR REPELLING BLOOD FEEDING ARTHROPODS AND APPARATUS FOR DETERMINING REPELLENCY AND ATTRATANCY OF SEMIOCHEMICALS AGAINST AND FOR BLOOD FEEDING ARTHROPODS

[75] Inventors: Jerry F. Butler, Gainesville, Fla.; Craig B. Warren, Rumson, N.J.; Anna B. Marin, Leonardo, N.J.; Braja D. Mookherjee, Holmdel, N.J.; Richard A. Wilson, Westfield, N.J.

[73] Assignees: International Flavors & Fragrances Inc., New York, N.Y.; The University of Florida, Gainesville, Fla.

[21] Appl. No.: 157,419

[22] Filed: Nov. 26, 1993

Related U.S. Application Data

[60] Division of Ser. No. 7,287, Jan. 21, 1993, Pat. No. 5,327,675, which is a continuation-in-part of Ser. No. 887,138, May 22, 1992, Pat. No. 5,228,233.

[51] Int. Cl.$^6$ .................... A01N 35/06; A01N 31/06; A01N 31/00
[52] U.S. Cl. .................... 514/690; 514/729; 514/730; 514/919; 252/107; 512/4; 424/DIG. 10
[58] Field of Search ............... 514/690, 729, 730, 919; 252/106, 107; 424/405, 409, DIG. 10; 512/4

[56] References Cited

U.S. PATENT DOCUMENTS

| | | | |
|---|---|---|---|
| 2,564,665 | 8/1951 | Bartlett et al. | 514/729 |
| 4,219,570 | 8/1980 | Inazuka et al. | 514/731 |
| 4,992,270 | 2/1991 | Wilson et al. | 424/84 |
| 5,270,345 | 12/1993 | Coulston | 514/756 |

*Primary Examiner*—Allen J. Robinson
*Assistant Examiner*—John D. Pak
*Attorney, Agent, or Firm*—Arthur L. Liberman

[57] ABSTRACT

Described is a method for repelling at least one of the insect species:
 (a) *Musca domestica* L. (Diptera:Muscidae);
 (b) *Aedes aegypti;*
 (c) *Aedes albopictus;*
 (d) *Anopheles* spp.
 (e) *Coquillettidia perturbans;*
 (f) *Culiseta* spp.;
 (g) *Culex* spp.;
 (h) *Psorophora* spp.;
 (i) *Culicoides* spp.; and/or
 (j) *Lutzomyia* spp.

for a finite period of time from a three dimensional space comprising the step of exposing the three dimensional space to an insect species (as named above) concentration and quantity of an alkylcyclopentanone having the structure:

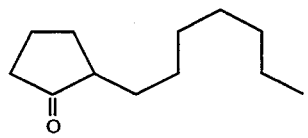

or a phenylalkanol derivative having the structure having the structure:

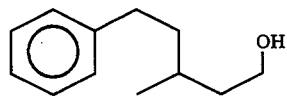

or mixtures of one of the above compounds with mixtures of cycloalkanol derivatives produced according to U.S. Pat. No. 4,275,251 issued on Jun. 23, 1981.

6 Claims, 27 Drawing Sheets

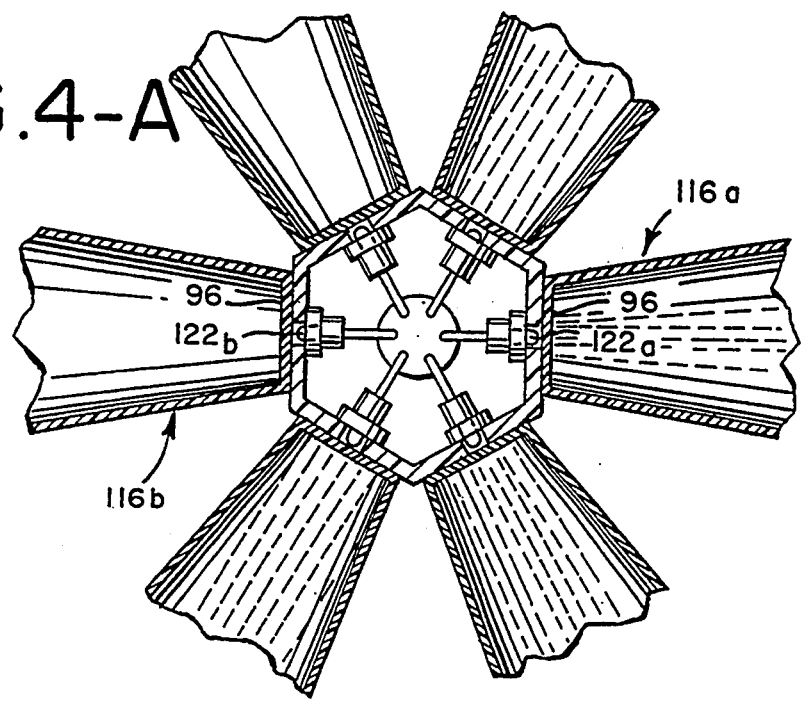
FIG.4-A
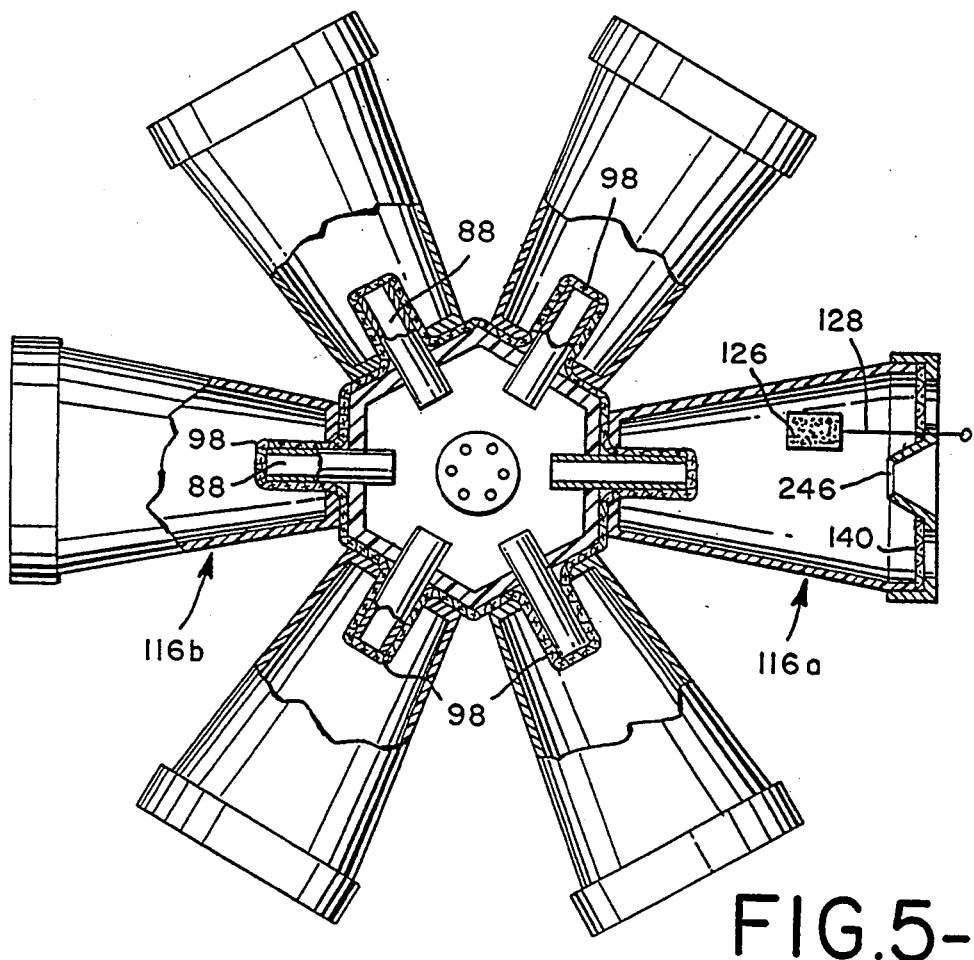
FIG.5-A

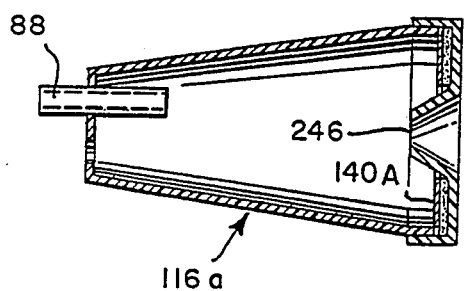
FIG. 8
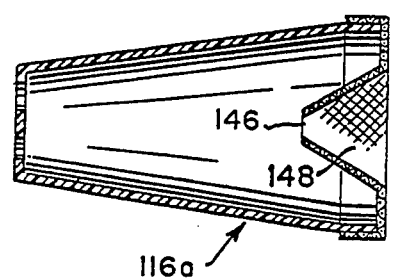
FIG. 9
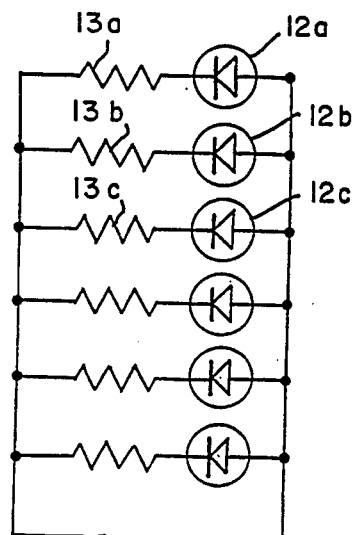
FIG. 7
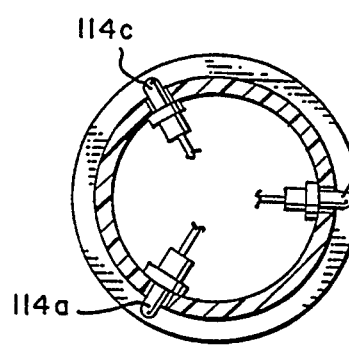
FIG. 6
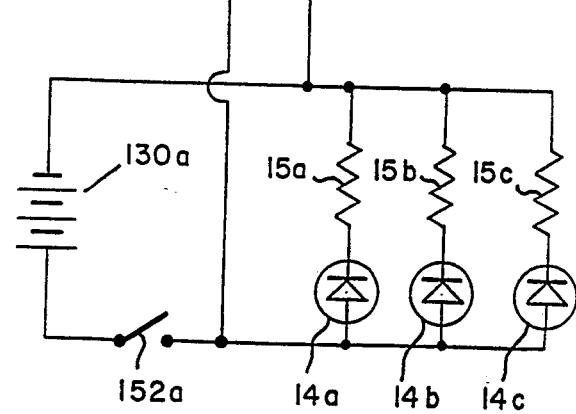

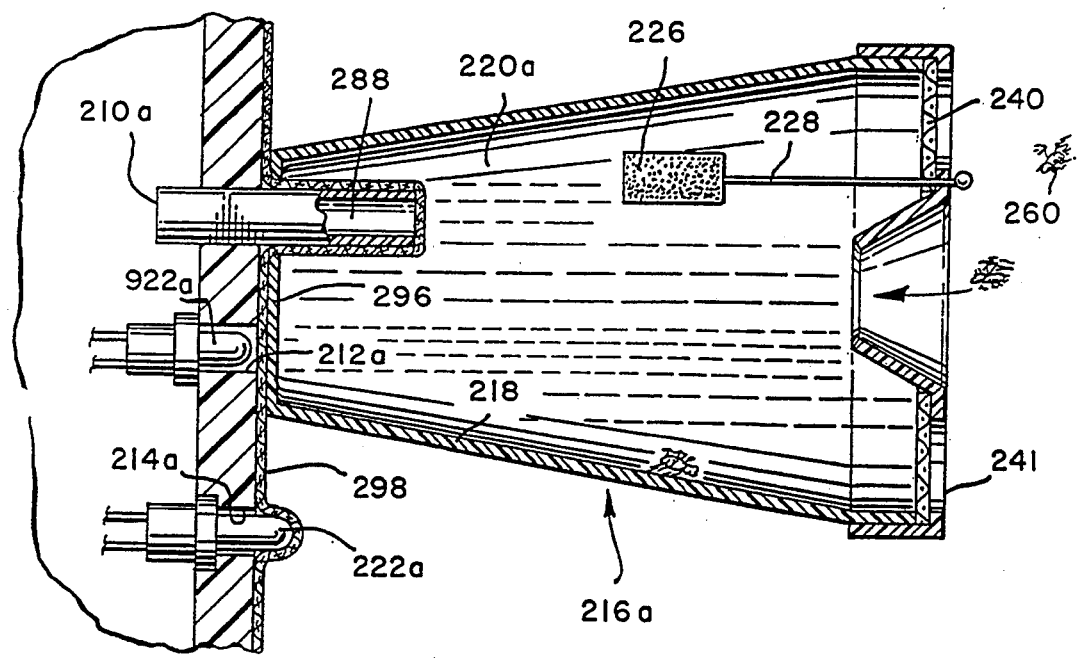
FIG.10-A
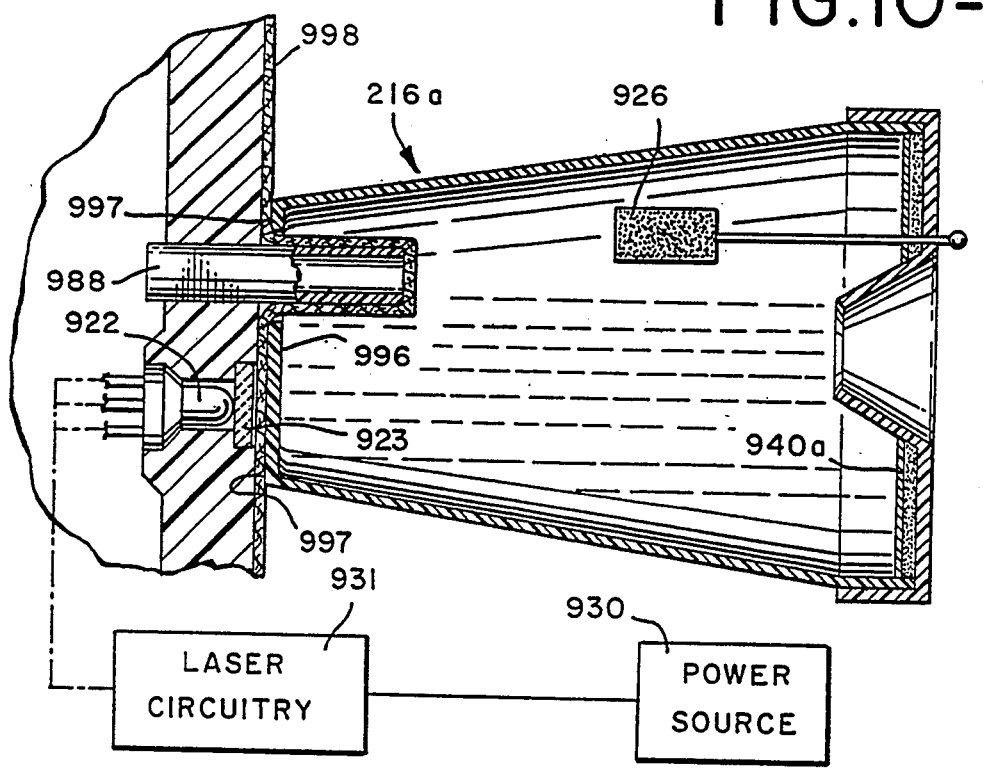
FIG.10-B

FIG.13
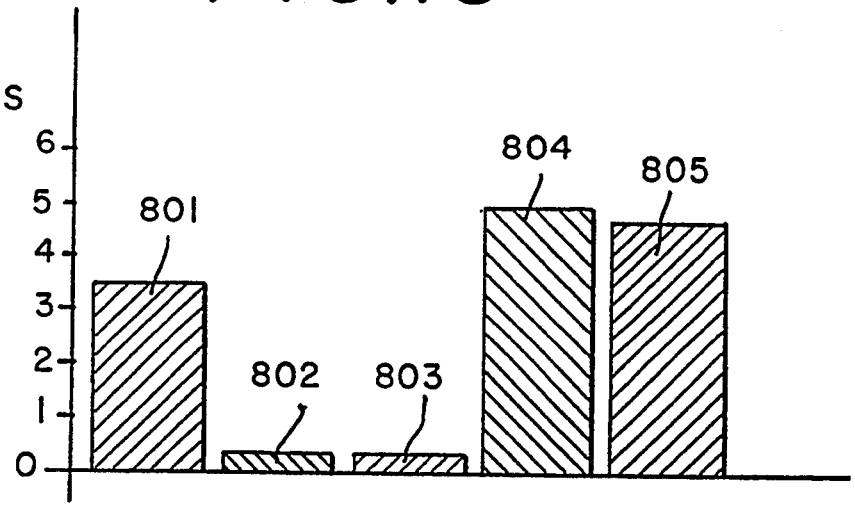
FIG.14-A
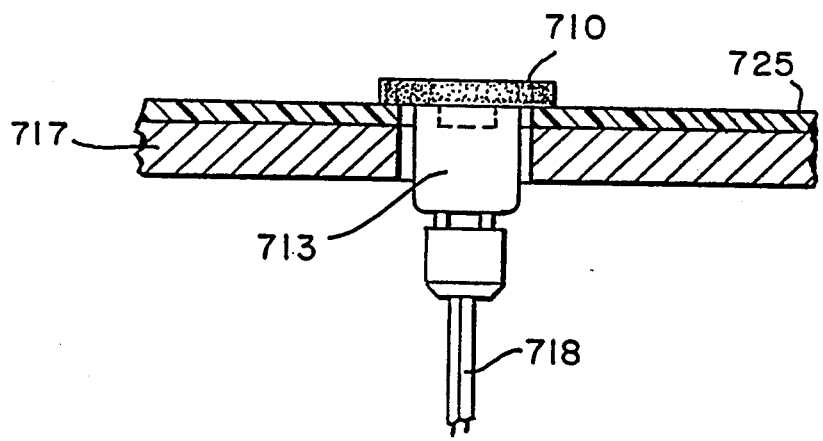

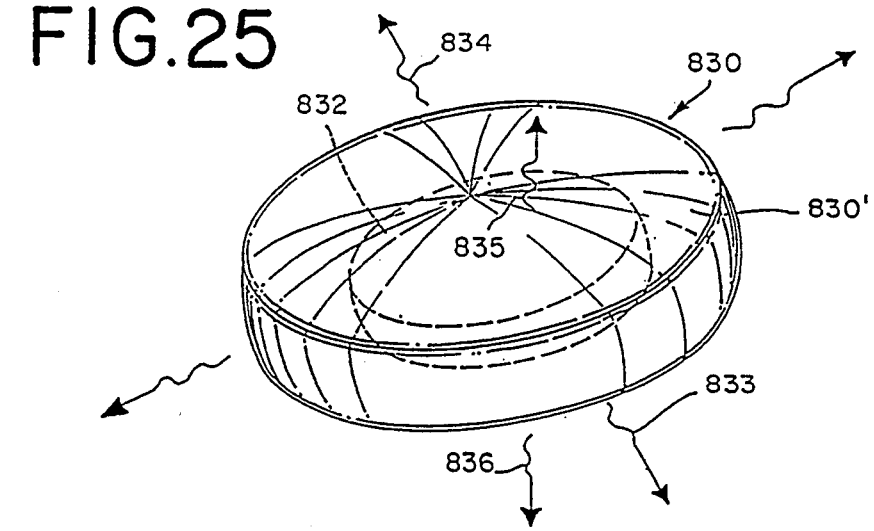
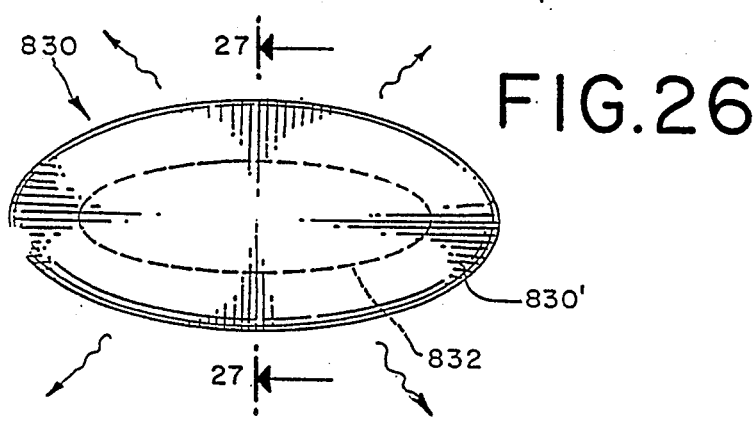
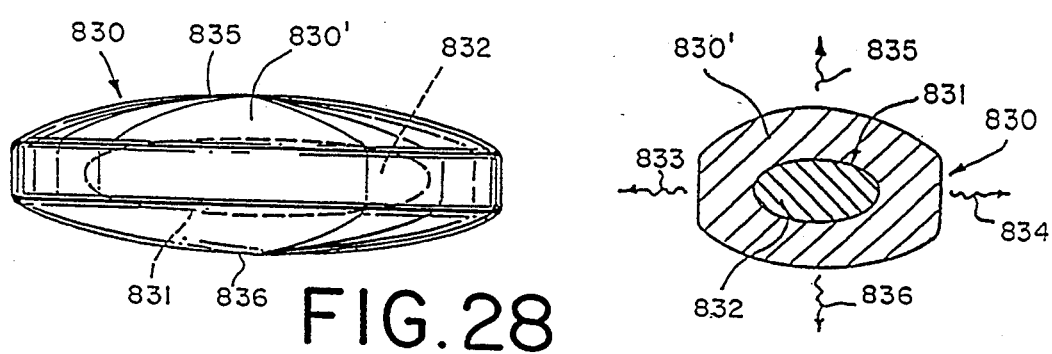

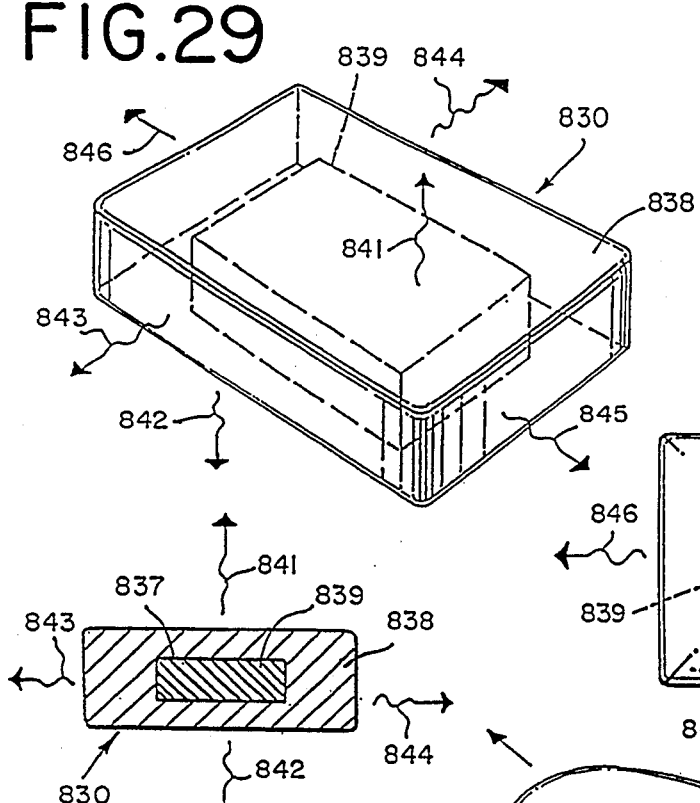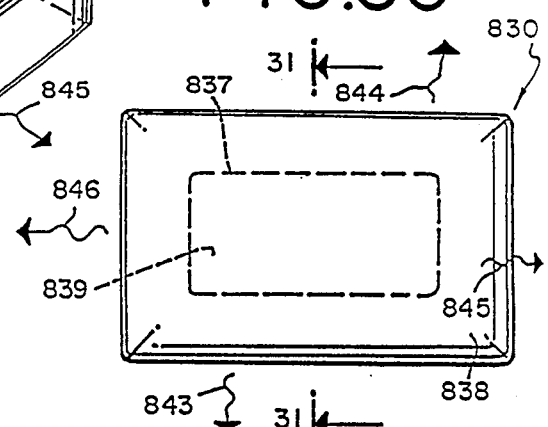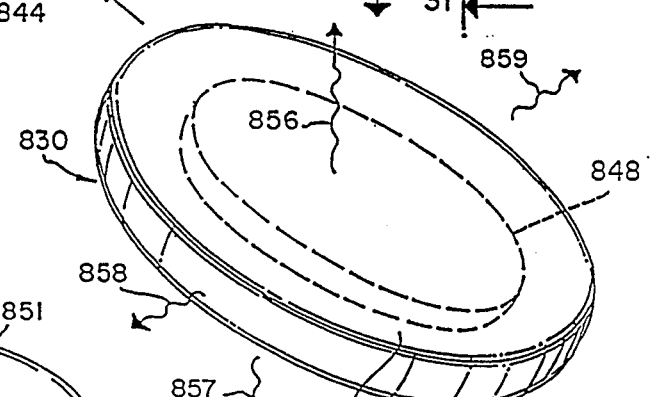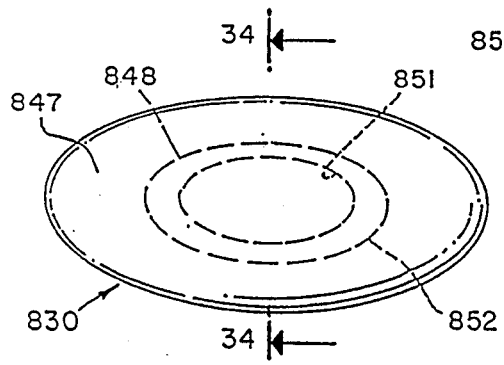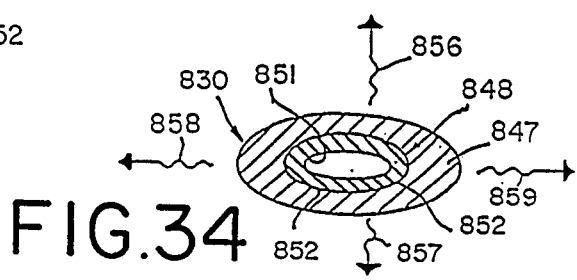

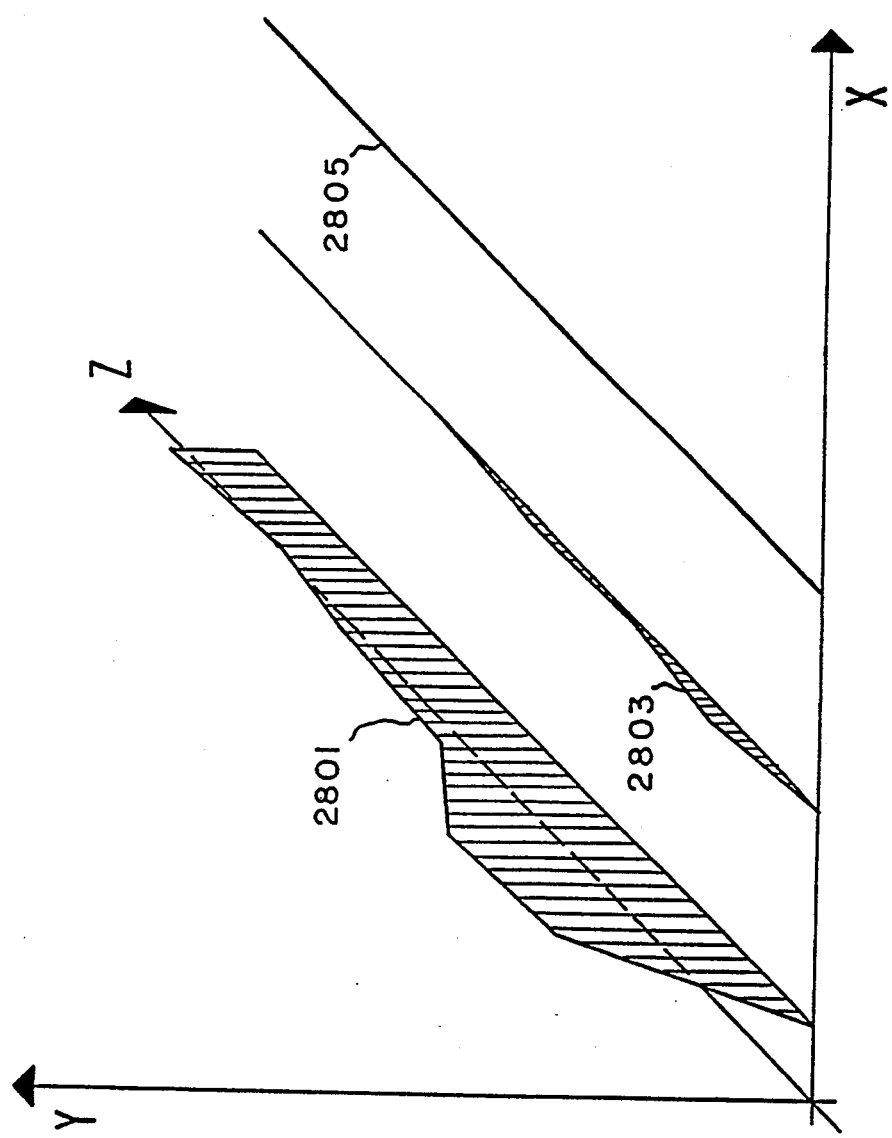

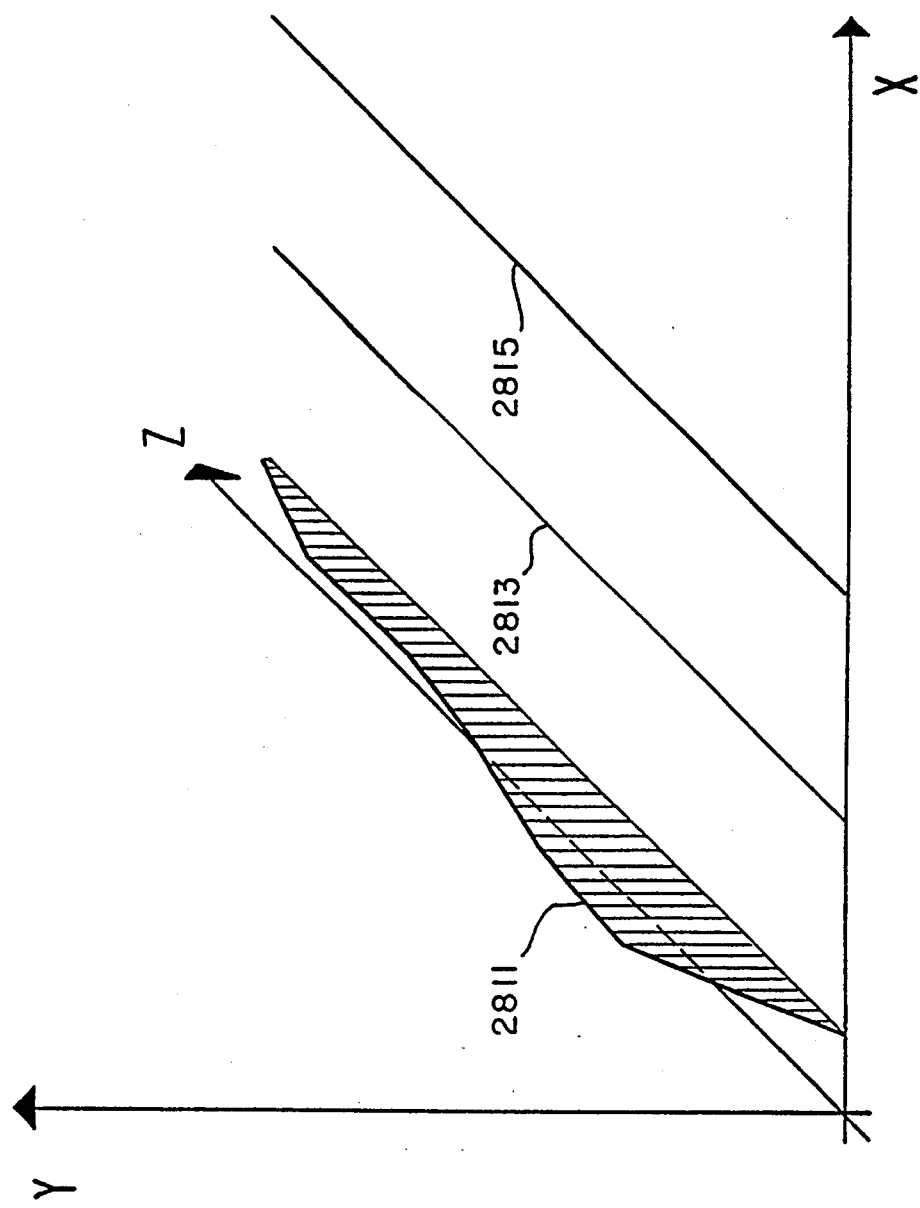
FIG.36-B

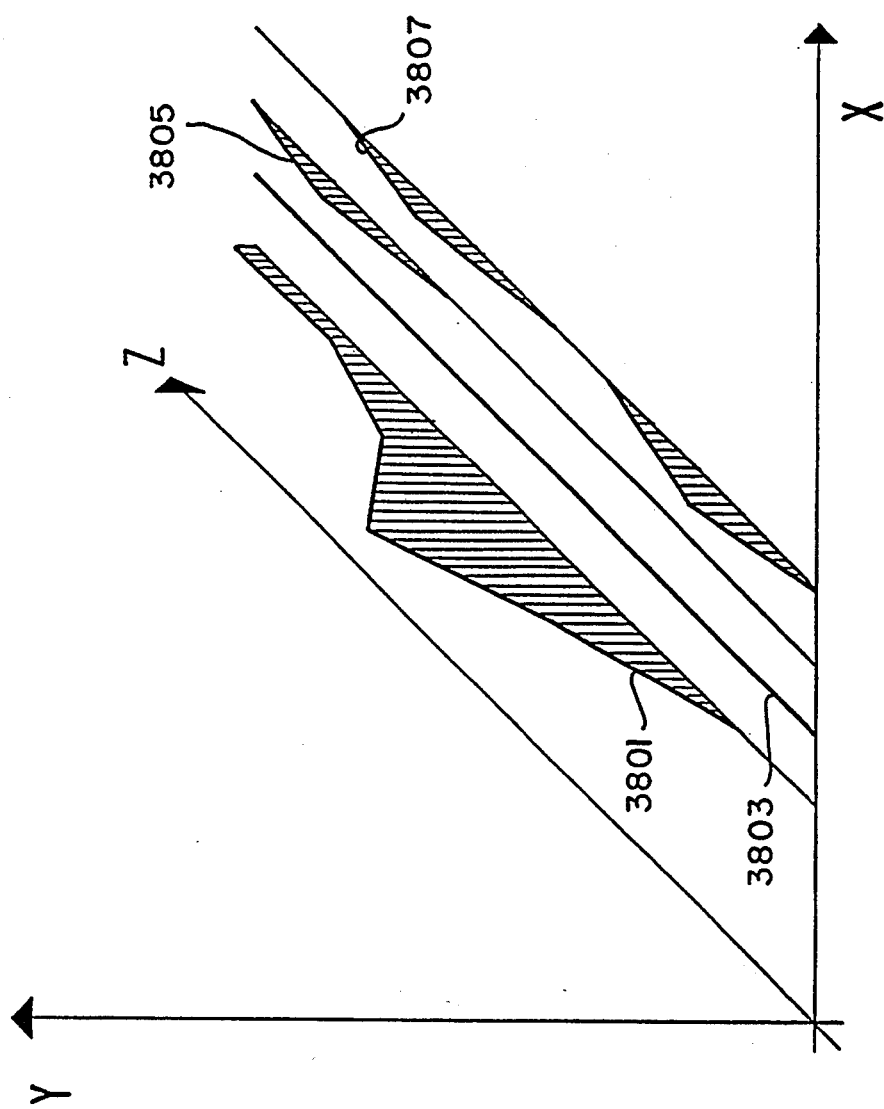

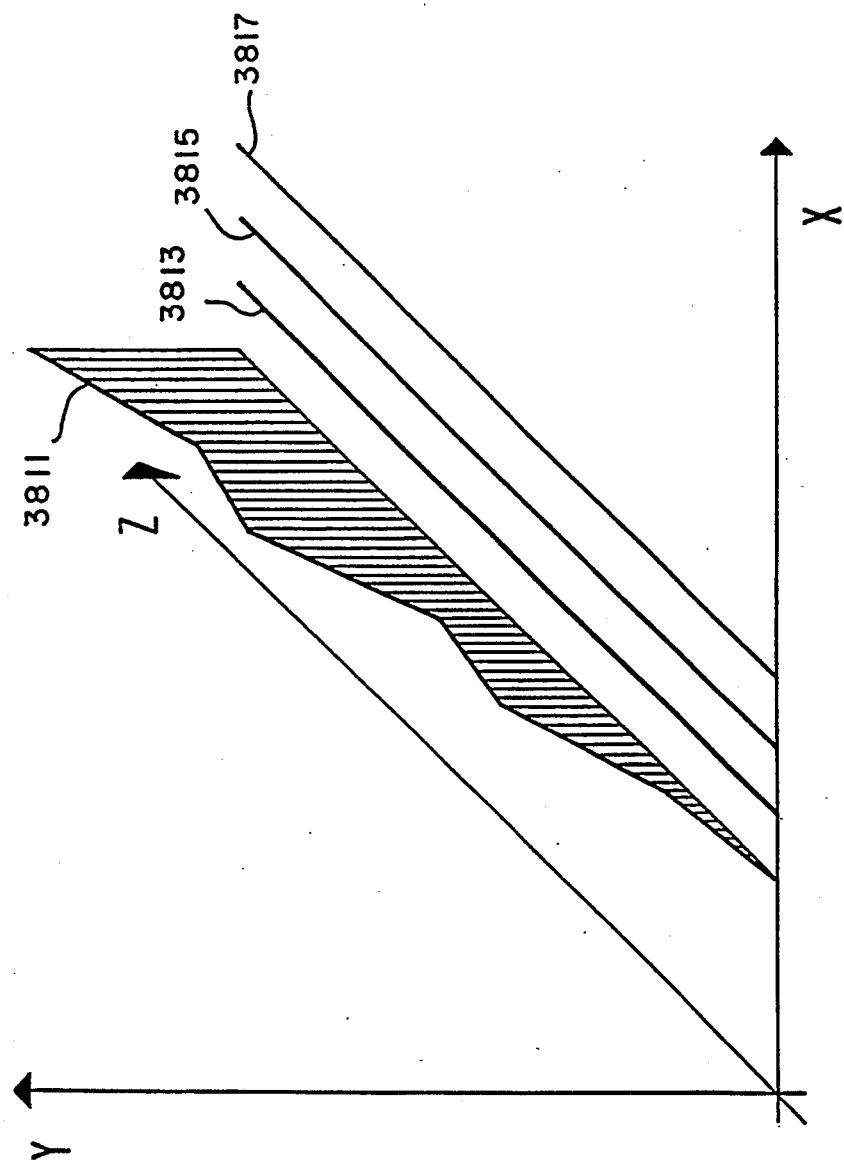

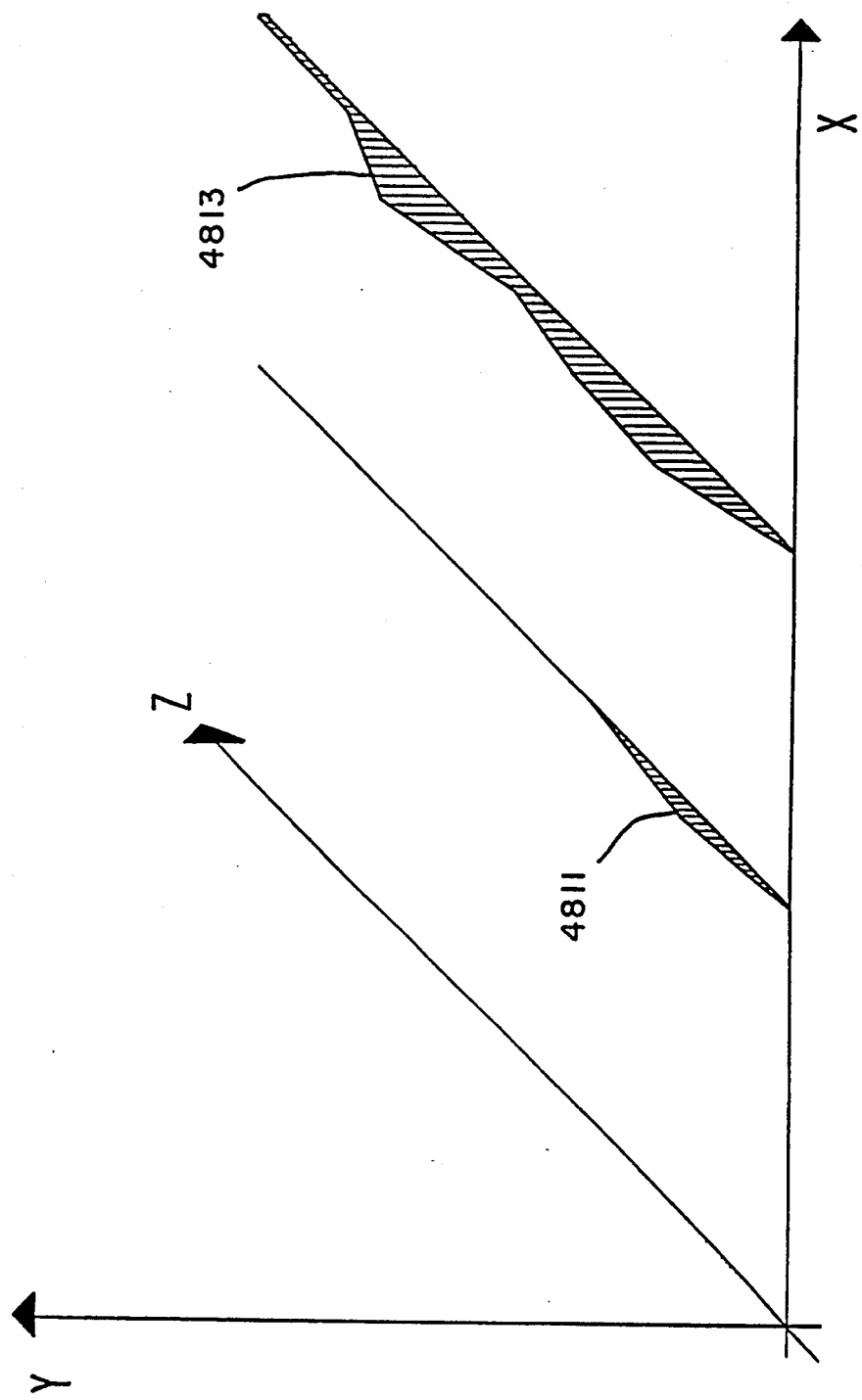

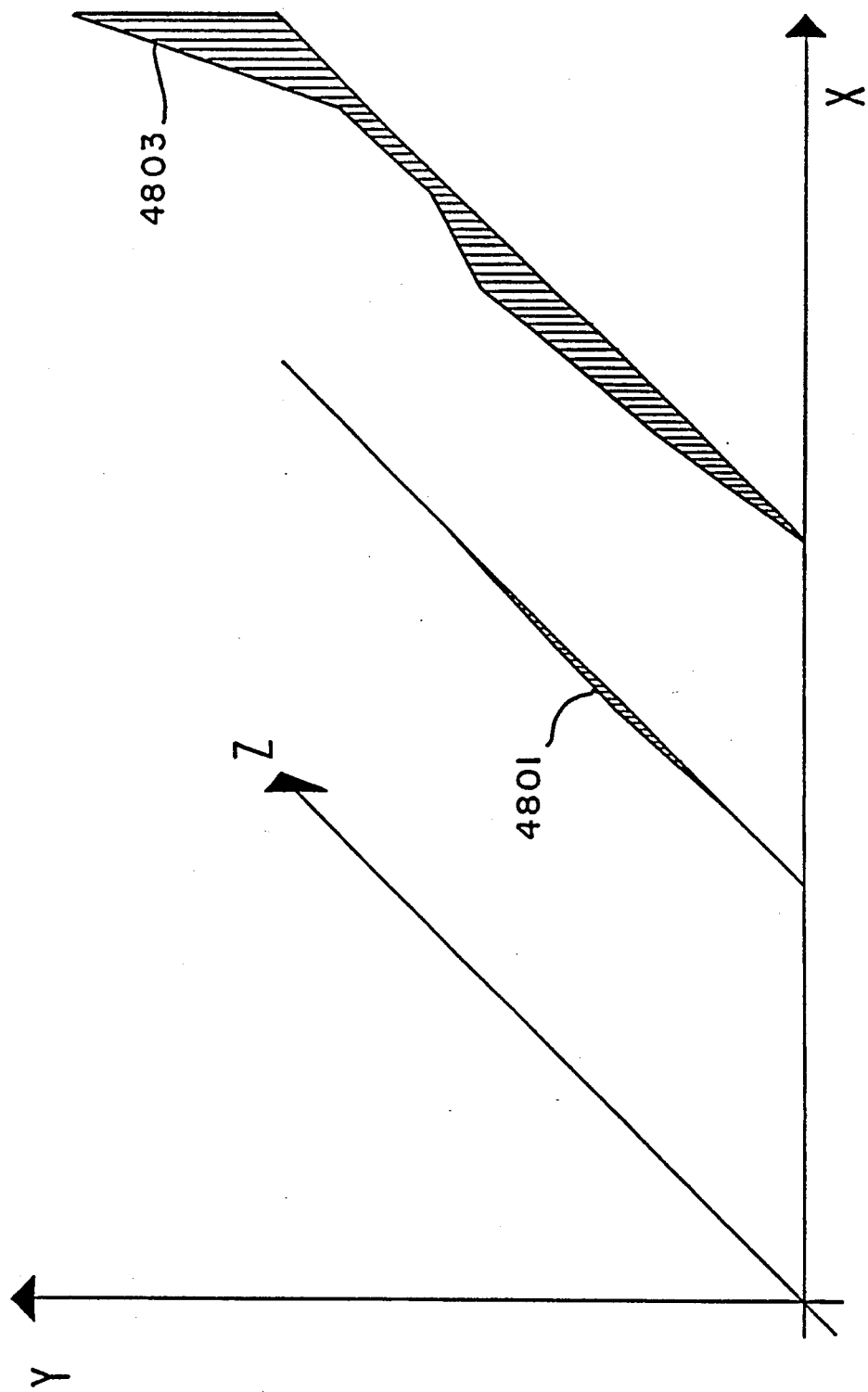
FIG.38-B

USE OF ALKYL CYCLOPENTANONE AND PHENYL ALKANOL DERIVATIVE-CONTAINING COMPOSITIONS FOR REPELLING BLOOD FEEDING ARTHROPODS AND APPARATUS FOR DETERMINING REPELLENCY AND ATTRATANCY OF SEMIOCHEMICALS AGAINST AND FOR BLOOD FEEDING ARTHROPODS

This application is a divisional of application for U.S. patent Ser. No. 08/007,287, filed on Jan. 21, 1993, now U.S. Pat. No. 5,327,675, issued on Jul. 12, 1994 which, in turn, is a continuation-in-part of application for U.S. patent Ser. No. 887,138, filed on May 22, 1992, now U.S. Pat. No. 5,228,233, issued on Jul. 20, 1993.

BACKGROUND OF THE INVENTION

Our invention relates to the use of alkyl cyclopentanone and phenyl alkanol derivative-containing compositions having the structures:

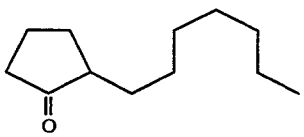

or

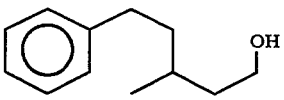

taken alone, in admixture or in admixture with the cycloalkanol derivative-containing compositions containing the compounds having the structures:

and

for repelling blood feeding arthropods, including species of mosquitoes and house flies as well as apparatus for determining repellency and attractancy of semiochemicals such as the aforementioned cycloalkanol derivative-containing compositions against and for such blood feeding arthropods.

Alkanols are known for repelling insects and the prior art contains many references pertaining to same. Thus, the use of 1-nonen-3-ol as a repellent is disclosed in U.S. Pat. No. 4,759,228 issued on Jul. 26, 1988, as a repellent for house flies (*Musca domestica L.*(Diptera:-Muscidae)).

Nothing in the prior art, however, sets forth the unexpected, unobvious and advantageous properties of the alkyl cyclopentanone and phenyl alkanol derivative-containing compositions of our invention so useful in repelling the species of insects set forth herein.

Furthermore, the prior art is replete with references showing various traps for insects, including said U.S. Pat. No. 4,759,228 issued on Jul. 26, 1988. Other prior art showing such insect traps is:

Griffiths and Bowman, Acarology VI, Volume 2, published by Ellis Horwood Limited §15.5, "Sampling Techniques For Burrow-Dwelling Ticks In Reference To Potential African Swin Fever Virus Vectors" (Butler, et al).

Garcia R., (1962), Ann.Entomol.Soc.Amer., 55 605–606.

Garcia R., (1965), Amer.J.Trop. Med.Hyg., 14 1090–1093.

Hair, J. A., Hoch, A. L., Barker, R. W., & Semtner, P. J., (1972), J.Med.Entomol., 9 153–155.

Holscher, K. H., Gearhart, H. L. & Barker, R. W. (1980) Ann.Entomol.Soc.Amer., 73 288–292.

Koch, H. G. & McNew, R. W., (1981), Ann.Entomol.Soc.Amer., 74, 498–500.

Nothing in the prior art sets forth the trap of our invention.

SUMMARY OF THE INVENTION

Our invention is directed to a semiochemical field trap for blood feeding arthropods which has the capability of causing determination of repellency and attractancy of semiochemicals against and for blood feeding arthropods. The field trap comprises:

(1) An upright vertically disposed hollow housing means: having arthropod-impenetrable vertical side wall means defining a vertically disposed inner void, (for example, a cylindrical rigid plastic housing produced from a phenol-formaldehyde polymer); having an upper terminal end means provided with gas entry means; having and piercing said side wall means, at least two horizontally-disposed separate sets of apertures, including an aperture set $S_1$ and an aperture set $S_2$; with aperture set $S_1$ being vertically distant from and substantially adjacent to aperture set $S_2$; with the apertures of aperture sets $S_1$ and $S_2$ being gas transmission apertures containing gas transmission means (e.g., a polyethylene tube) or having first radiation means sealably inserted therethrough (for example, a light emitting diode or a laser diode);

(2) Horizontally disposed hollow housing means (for example, horizontally disposed open ended hollow cylinders fabricated from aluminum or rigid plastic such as acrylic plastic) having substantially horizontally disposed arthropod impenetrable side walls defining horizontally disposed inner void means; having oppositely juxtaposed inner and outer open terminal end means; the inner terminal end means being circumferentially sealably contiguous with a portion of the outer surface of said vertical side wall means of said upright housing means which portion circumscribes a section of the vertical side wall means including at least one aperture of aperture set $S_1$ and at least one aperture of aperture set $S_2$, one of the apertures being a gas transmission aperture containing the gas transmission means (e.g., the polyethylene tubing) and the other of the apertures having sealably contained therethrough radiation means (for example, the light emitting diode or the laser diode); having incorporated into the inner structure thereof arthropod entrapment means (for example, a sticky insect trapping substance as disclosed in the prior art) and having a sustainably releasable insect attractant or repellent semiochemical substance means located within (i) said horizontally disposed inner void means or (ii) said gas transmission means, for example, a matrix comprising a porous containment agent (e.g., polyethylene, polypropylene, a polyamide, a polyurethane or the like) containing in the interstices thereof at least one semiochemical sustainably releasable therefrom (e.g., the cycloalkanol substance-containing composition of our invention) or, for example, the substances and structures described at columns 13, 14 and 15 of U.S. Pat. No. 4,748,860 issued on Jun. 7, 1988 the specification for which is incorporated by reference herein;

(3) Gas transmission effecting means for causing conveyance of a gas (such as air or carbon dioxide) through said gas entry means into and through said vertically disposed inner void, through a gas transmission aperture of aperture set $S_1$ and/or of aperture set $S_2$ into and through said horizontally disposed inner void means and into the environment surrounding the field trap (for example, such gas transmission effecting means can be a carbon dioxide gas supply means for supplying gasous carbon dioxide simultaneously with the operation of power supply means);

(4) optionally second radiation means located within said vertically disposed inner void for conveying insect attracting radiation through substantially each of said gas transmission apertures of aperture set $S_1$ and/or aperture set $S_2$;

(5) radiation pulsing means connected to said first radiation means and/or said second radiation means causing said first insect attracting radiation and/or said second insect attracting radiation to have a frequency mimicking insect wing beat and/or insect visual sensing frequencies;

(6) at least one power supply means associated with the trap at least energizing the first and second radiation means and the radiation pulsing means;

whereby on engagement of the power supply means with the radiation effecting means and simultaneous activation of the gas transmission effecting means and the radiation pulsing means, blood feeding arthropods in the vicinity of the trap are attracted by (i) activated radiation emitted by the radiation means and/or (ii) gas emanating from the outer open terminal end means of the horizontally disposed hollow housing means to a location so close to the trap that in the event that an attracting semiochemical in the sustainably releasable substance means is detected and attracts at least one of the arthropods, such arthropods will enter the horizontally disposed inner void means counter-current to the flow of the emanating gas or gaseous ion (e.g., $CO_2$ or ion) and will remain permanently entrapped therein (usually as a result of a sticky substance adhering to the inner portion of the horizontally disposed housing(s)).

It is preferable when using the radiation emission means, to use infra-red light. Control experiments are preferably run using carbon dioxide with the use of infra-red radiation lights (light emitting diodes) and without the use of infra-red radiation lights. However, experiments using the trap may also be carried out with other lights such as bright green lights and blue lights (in the form of light emitting diodes). In both cases the radiation emission means utilizes preferably the circuit of FIG. 11 or FIG. 12 described, infra. Other circuits are used when using laser diodes instead of light emitting diodes. An example of the green light being used is one manufactured by the Marktech International Corporation of Menands, N.Y., Catalog Part No. MT300-CUG (T-1.75 water clear ultra-bright green light emitting diode lamp). When using infra-red radiation means, it is preferable to utilize a gallium arsenide infra-red light emitting diode such as Model MTE 1080 gallium arsenide emitter manufactured by Marktech of 120 Broadway, Menands, N.Y. 12204. When using a laser diode, laser diodes such as those marketed under Catalog Nos. P451 or P452 by the DIGI-KEY ® Corporation of 701 Brooks Avenue South, P.O. Box 677, Thief River Falls, Minn. 56701-0677 are useful and operable.

The radiation pulsing means is intended herein to be a flicker fusion frequency generator to present a frequency of from about 50 up to about 400 cycles per second (Herz). Such frequencies are intended to mimic blood feeding arthropod wing beat frequencies and visual sensing frequencies. The radiation pulsing means is intended to cause the firing of, for example, radiation emitting diodes having a range of from about 400 up to about 1000 nm (nanometers).

The radiation pulsing means can be in the form of a direct radiation stroblight such as that illustrated in FIG. 17 or it can be in the form of an off-apparatus stroblight unit which causes radiation pulsing to be conveyed through fiber optic strands as set forth, for example, in FIG. 19, described, infra.

In any event, radiation pulsing means which can be used in the practice of our invention are set forth in the following publications:

(i) published Canadian Patent Application 2,040,615 published on Oct. 17, 1992 (title: "Cel-Alert' An Easy To-Use Emergency Strobe-Light Road Safety Device");

(ii) the Stroboscope/Tachometer marketed by the Edmund Scientific Company of Barrington, N.J.;

(iii) the "Realistic Wide Angle Strobe Light" Catalog No. 42-3009A marketed by the Radio Shack Division of Tandy Corporation of Ft. Worth, Tex.;

(iv) the Enerlite Personal Strobe, Catalog No. 61-2506 marketed by the Radio Shack Division of Tandy Corporation of Ft. Worth, Tex.

Other light emitting diodes that are useful in the practice of our invention are, for example, those set forth in Canadian Published Patent Application 2,065,577 published on Oct. 17, 1992 entitled "Encapsulated Light Emitting Diode And Method For Encapsulation".

When preparing the semiochemical matrix which is preferably a block, 10 microliters of test material, e.g., the alkyl cyclopentanone and phenyl alkanol derivative-containing compositions of our invention are soaked onto a 9 mm×9 mm×9 mm block.

The carbon dioxide supply source is most conveniently dry ice placed in a "zippered" bag (with a TYGON ® tubing outlet). The dry ice is placed in a zippered bag and the bag is then placed in an insulated ice chest. Preferably between 4 and 5 kilograms of dry ice is used, preferably in the form of pellets or blocks.

On placing the trap in the test. area, the motor means is engaged with the power supply means, preferably, simultaneously, with the engagement of the radiation means with the power supply means. Thus, at the instant that the trap is commenced to be in use, the air flow creation means (e.g., a propeller) begins its rotation simultaneously with the radiation means being energized and with the motor means being energized. Thus, arthropods, e.g., mosquitoes and house flies as set forth, supra, in the vicinity of the trap are attracted by the radiation to a location so close to the trap that in the event that an attracting semiochemical in the matrix is detected by the arthropods, the arthropods will enter the air stream or the $CO_2$ stream created by the air flow creation means, e.g., the propeller or the $CO_2$ flow or both and be carried into the 3-space within the horizontally disposed hollow housing means. Once within the trap the arthropods will not . escape in view of the fact that they are in the vicinity of such gas as carbon dioxide being emitted by the carbon dioxide supply source and they are in the vicinity of radiation emitted by radiation emission means and are attracted thereto. Furthermore, in the event of the presence of a sticky substance within the horizontally disposed hollow housing means, they are trapped by a sticky substance known in the prior art.

The traps are usually run for a period of from about 36 hours up to about 40 hours. They are set up in usually linear transects across flight ranges replicated (6–12 replications) about 10 meters apart.

The gas transmission means transmitting gas from the vertically disposed hollow housing to the horizontally disposed hollow housing (e.g., TYGON ® tubing) requires a screen or mesh substance at the orifice thereof within the horizontally disposed hollow housing means. Preferably, a nylon mesh is used which nylon mesh extends entirely around the upright vertically disposed hollow housing means covering each of the gas transmission means (e.g., TYGON ® tubing orifices). Preferably, the mesh size of the mesh (e.g., nylon mesh) used for this purpose should range from about 10 up to about 200 lines per inch and thus, for example, may be 20/6 T-66 textured nylon or 70/32 polyester (e.g., a polymer of phthalic anhydride and ethylene glycol).

Our invention is also directed to a method for repelling at least. one of the insect species:

(a) *Musca domestica L.*(Diptera:Muscidae);
(b) *Aeries aegypti;*
(c) *Aedes albopictus;*
(d) Anopheles spp.;
(e) *Coquillettidia perturbans;*
(f) Culiseta spp.;
(g) Culex spp.;
(h) Psorophora spp.;
(i) Culicoides spp.; and/or
(j) Lutzomyia spp.

for a finite period of time from a three dimensional space comprising the step of exposing said three dimensional space to a:

(a) *Musca domestica L.*(Diptera: Muscidae);
(b) *Aedes aegypti;*
(c) *Aedes albopictus;*
(d) Anopheles spp.;
(e) *Coquillettidia perturbans;*
(f) Culiseta spp.;
(g) Culex spp.;
(h) Psorophora spp.;
(i) Culicoides spp.; and/or
(j) Lutzomyia spp.

of a composition of matter which is an alkyl cyclopentanone or phenyl alkanol derivative-containing composition of matter having the structure:

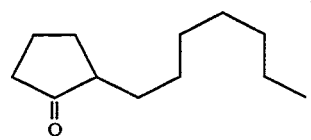

or

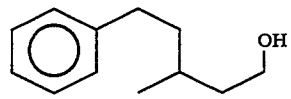

taken alone, or in combination, or further in combination with a mixture of cycloalkanol derivatives having the structures:

and

produced by means of a process of reacting a lower alkanoic acid with methyl cyclopentadiene dimer which is a mixture of compounds having the structures:

and

in the presence of a protonic acid such as sulfuric acid or a Lewis acid such a boron trifluoride etherate; and then saponifying the resulting product with base such as aqueous 50% sodium hydroxide in accordance with the process of Examples I, II, III, IV and V of U.S. Pat. No. 4,275,251 issued on Jun. 23, 1981 the specification for which is incorporated by reference herein.

Our invention is also directed to the use of an insect repelling soap which can on use thereof cause the repellents from the user of any of the species of insects set forth above comprising a soap base and in intimate contact therewith, an alkylcylopentanone or phenylalkanolderivative having the structure:

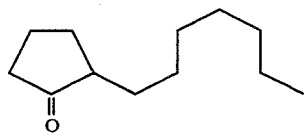

or

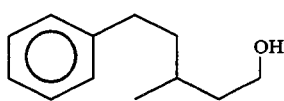

taken alone or in combination or in further combination with a mixture of cycloalkanol derivatives having the structures:

and

Such soap articles can be prepared according to the specification of Application for U.S. patent, Ser. No. 824,591 filed on Jan. 23, 1992, now U.S. Pat. No. 5,205,065, the specification for which is incorporated herein by reference.

Our invention is also directed to insect repelling perfume bases which can on use thereof effect repellents from the user of any of the species of insects set forth above comprising a perfume base and intimately admixed therewith an alkyl cyclopentanone or phenyl alkanol derivative-containing composition having the structure:

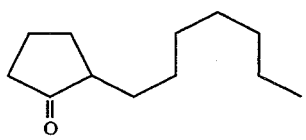

or

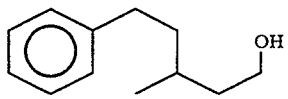

taken alone or in combination or in further combination with a mixture of cycloalkanol derivatives having the structures:

and

Such insect repelling perfume bases can be prepared according to the teachings of Application for U.S. patent, Ser. No. 691,635 filed on Apr. 25, 1991 (now abandoned), the specification for which is incorporated by reference herein.

The insect repelling articles containing the alkyl cyclopentanone or phenylalkanol derivative-containing compositions of our invention taken alone or further in combination with the mixture of cycloalkanol derivatives useful for repelling the insect species set forth, supra, may be produced according to processes set forth at columns 12, 13, 14 and 15 of U.S. Pat. No. 4,748,860 issued on Jun. 7, 1988 the specification of which is incorporated herein by reference.

In addition to using the field trap apparatus of our invention, olfactometer apparatus of, for example, U.S. Pat. No. 4,748,860 of Jun. 7, 1988 may be used in testing the materials for their insect attractancy or repellency, for example, the apparatus of FIG. 14 described in detail, infra.

Accordingly, the following Tables I-V(B), inclusive, show the results of utilization of the olfactometer apparatus of FIG. 14 in testing for the attractancy or repellency of *Musca domestica* L.(Diptera:Muscidae) and *Aedes aegypti* using both (i) the cycloalkanol derivative-containing composition of matter of patent application, Ser. No. 887,138 filed on May 22, 1992 now U.S. Pat. No. 5,228,233 (versus bay leaf oil and clean air); and (ii) the alkyl cyclopentanone or phenylalkanol derivative-containing compositions of our invention (versus clean air):

TABLE I

| *AEDES AEGYPTI* | | | | | | | |
|---|---|---|---|---|---|---|---|
| COMPOSITION TESTED | INSECTS PER INTERVAL | | | | | | |
| Air | 0 | 275 | 375 | 417 | 373 | 359 | 321 |

TABLE I-continued

AEDES AEGYPTI

| COMPOSITION TESTED | INSECTS PER INTERVAL | | | | | | |
|---|---|---|---|---|---|---|---|
| Bay Leaf Oil | 0 | 4 | 5 | 14 | 0 | 1 | 1 |
| Cycloalkanol Derivative Containing Composition of U.S. Pat. application, Ser. No. 887,138 filed on May 22, 1992 now U.S. Pat. No. 5,228,233 | 0 | 1 | 0 | 0 | 0 | 0 | 0 |

TABLE II

MUSCA DOMESTICA L. (DIPTERA:MUSCIDAE)

| COMPOSITION TESTED | INSECTS PER INTERVAL | | | | | | |
|---|---|---|---|---|---|---|---|
| Air | 0 | 0 | 62 | 1 | 1 | 1 | 19 |
| Bay Leaf Oil | 0 | 0 | 1 | 0 | 0 | 0 | 1 |
| Cycloalkanol derivative-containing composition of U.S. Pat. application, Ser. No. 887,138 filed on May 22, 1992 now U.S. Pat. No. 5,228,233 | 0 | 0 | 2 | 0 | 0 | 1 | 1 |

TABLE III(A)

AEDES AEGYPTI (ONE HOUR)

| COMPOSITION TESTED | INSECTS PER INTERVAL | | | | | | | |
|---|---|---|---|---|---|---|---|---|
| Air | 464 | 486 | 263 | 242 | 137 | 253 | | |
| Compound having the structure: | 0 | 52 | 1 | 11 | 0 | 0 | 0 | |

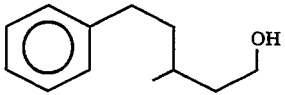

| | | | | | | | | |
|---|---|---|---|---|---|---|---|---|
| Cycloalkanol derivative-containing composition of Parent Application Ser. No. 887,138 filed on May 22, 1992, now U.S. Pat. No. 5,228,233 | 0 | 0 | 0 | 0 | 0 | 0 | 0 | 0 |

TABLE III(B)

AEDES AEGYPTI (SIX HOURS)

| COMPOSITION TESTED | INSECTS PER INTERVAL | | | | | | |
|---|---|---|---|---|---|---|---|
| Air | 0 | 253 | 231 | 162 | 117 | 125 | 16 |
| Composition having the structure: | 0 | 0 | 3 | 5 | 2 | 3 | 2 |

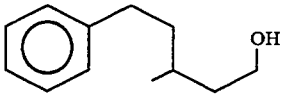

| | | | | | | | |
|---|---|---|---|---|---|---|---|
| Cycloalkanol derivative-containing composition of Parent Application, Ser. No. 887,138 filed on May 22, 1992 now U.S. Pat. No. 5,228,233 | 0 | 0 | 0 | 0 | 0 | 0 | 0 |

TABLE IV(A)

AEDES AEGYPTI (ONE HOUR)

| COMPOSITION TESTED | INSECTS PER INTERVAL | | | | | | |
|---|---|---|---|---|---|---|---|
| Air | 0 | 4 | 93 | 213 | 77 | 25 | 28 |
| Cycloalkanol derivative-containing composition of Parent Application, Ser. No. 887,138 filed on May 22, 1992, now U.S. Pat. No. 5,228,233 | 0 | 5 | 0 | 0 | 0 | 0 | 0 |
| Composition having the structure: | 0 | 4 | 7 | 0 | 2 | 37 | 1 |

TABLE IV(A)-continued

AEDES AEGYPTI (ONE HOUR)

| COMPOSITION TESTED | INSECTS PER INTERVAL | | | | | | |
|---|---|---|---|---|---|---|---|
| 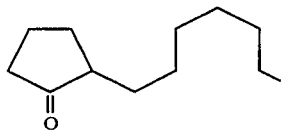 Composition having the structure: 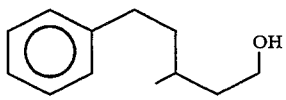 | 0 | 46 | 0 | 4 | 32 | 2 | 4 |

TABLE IV(B)

AEDES AEGYPTI (SIX HOURS)

| COMPOSITION TESTED | INSECTS PER INTERVAL | | | | | | |
|---|---|---|---|---|---|---|---|
| Air | 0 | 29 | 134 | 95 | 242 | 186 | 289 |
| Cycloalkanol derivative-containing composition of Parent Application, Ser. No. 887,138 filed on May 22, 1992 now U.S. Pat. No. 5,228,233 | 0 | 0 | 0 | 1 | 0 | 0 | 0 |
| Composition having the structure: 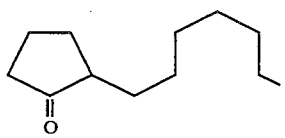 | 0 | 1 | 3 | 1 | 0 | 1 | 0 |
| Composition having the structure: | 0 | 4 | 4 | 1 | 2 | 1 | 4 |

TABLE V(A)

AEDES AEGYPTI (ONE HOUR)

| COMPOSITION TESTED | INSECTS PER INTERVAL | | | | | | |
|---|---|---|---|---|---|---|---|
| Air | 0 | 86 | 79 | 30 | 114 | 17 | 16 |
| Compound having the structure: | 0 | 36 | 0 | 0 | 0 | 0 | 0 |

TABLE V(B)

AEDES AEGYPTI (TWELVE HOURS)

| COMPOSITION TESTED | INSECTS PER INTERVAL | | | | | | |
|---|---|---|---|---|---|---|---|
| Air | 0 | 30 | 43 | 50 | 20 | 23 | 156 |
| Compound having the structure: | 0 | 0 | 12 | 7 | 3 | 1 | 0 |

TABLE V(B)-continued

AEDES AEGYPTI (TWELVE HOURS)

| COMPOSITION TESTED | INSECTS PER INTERVAL |
|---|---|
| 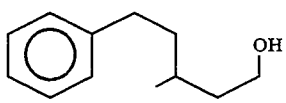 | |

DESCRIPTION OF THE DRAWINGS

FIG. 1A is a perspective schematic diagram of the axes in three dimensions used in defining the directional vectors and directions with which the apparatus of our invention is concerned.

FIG. 4A is a cut-away top view of a variation of the apparatus of FIG. 2 where the light emitting diodes are located behind a translucent end cover of the horizontally disposed hollow housing means of the apparatus.

FIG. 5A is a cut-away top view of a variation of the apparatus of FIG. 2 showing a mesh screen covering the orifices of the gas transmission means communicating between the void within the vertically disposed hollow housing means and the horizontally disposed hollow housing means.

FIG. 6 is a cut-away top view of the apparatus of FIG. 2 taken along lines 6—6.

FIG. 7 is an electric circuitry diagram of the electric circuit used to activate the radiation means 112A and 112B and 114A and 114B of FIG. 2.

FIG. 8 is a cut-away side elevation view of an embodiment of a horizontally disposed hollow housing means useful in the apparatus of FIGS. 2, 3 and 10.

FIG. 9 is a cut-away side elevation view of another embodiment of horizontally disposed hollow housing means used in the apparatus of FIGS. 2, 3 and 10.

FIG. 10A is a cut-away side elevation view, in detail, of that part of the apparatus of FIG. 10 which is concerned with the horizontally disposed hollow housing means; and shows a variation wherein the light emitting diode or laser diode is located behind a translucent end portion of the horizontally disposed hollow housing means.

FIG. 10B is a cut-away side elevation view of another embodiment of the horizontally disposed hollow housing means illustrated in FIG. 10A wherein the radiation emission means is shown as a laser diode having a diffusion lens between the laser diode and the horizontally disposed hollow housing means translucent end section.

FIG. 13 is a bar graph showing a comparison of the field trial tests in the semiochemical field trap for blood feeding arthropods of our invention of repellents against mosquitoes, e.g., Aedes aegypti, Aedes albopictus, Anopheles spp., Coquillettidia perturbans, Culiseta spp., Culex spp., and Psorophora spp., comparing in combination with the use of infra-red light emitting diodes and carbon dioxide, air alone, bay leaf oil, the cycloalkanol derivative-containing composition of Parent Application, Ser. No. 887,138 filed on May 22, 1992 now U.S. Pat. 5,228,233 lavender oil and vetiver oil.

FIG. 14A is a detailed section of the apparatus of FIG. 14 showing a specific landing site on which an insect lands if attracted by, for example, the cycloalkanol derivative-containing composition of Parent Application, Ser. No. 887,138 filed on May 22, 1992 now U.S. Pat. No. 5,228,233 or does not land if repelled by the cycloalkanol derivative-containing composition of Parent Application, Ser. No. 887,138 filed on May 22, 1992 now U.S. Pat. No. 5,228,233.

FIG. 25 is a perspective view of an ellipsoidally-shaped detergent tablet containing a solid core which includes fused foamed polymeric particles which contain insect repellents which can be one of the alkyl cyclopentanone or phenylalkanol derivative-containing compositions of our invention and if desired also containing an additional polymer, e.g., polyethylene. The polymer particles may, if desired, also contain additional aromatizing agents and insect repelling agents.

FIG. 26 is the top view of the ellipsoidally-shaped detergent tablet of FIG. 25.

FIG. 27 is a cut-away front view of the ellipsoidally-shaped detergent tablet of FIG. 25 in the direction of the arrows in FIG. 26.

FIG. 28 is a side view of the ellipsoidally-shaped detergent tablet of FIG. 26

FIG. 29 is a perspective view of a rectangular parallelpiped-shaped detergent tablet containing a rectangular parallelpiped-shaped core comprising a major proportion of fused foamed polymeric particles which contain insect repellents, (e.g., one or more of the alkyl cyclopentanone or phenylalkanol derivative-containing compositions of our invention) and may or may not be aromatized and, if desired, an additional polymer which may or may not contain insect repellent compositions and which may or may not be aromatized.

FIG. 30 is a top view of the rectangular parallelpiped-shaped detergent tablet of FIG. 29.

FIG. 31 is a cut-away front view of the rectangular parallelpiped-shaped detergent tablet of FIG. 29 looking in the direction of the arrows in FIG. 30.

FIG. 32 is a perspective view of an ellipsoidally-shaped detergent tablet containing a hollow insect repellent agent (and, if desired, an aromatizing agent) containing core which includes fused foamed polymeric particles (the insect repellent and, if desired, the aroma imparting agent is in the solid polymer and not in the void of the plastic core).

FIG. 33 is a top view of the ellipsoidally-shaped detergent tablet of FIG. 32.

FIG. 34 is a front cut-away view of the ellipsoidally-shaped detergent tablet of FIG. 32 looking in the direction of the arrows in FIG. 33, the core thereof being hollow and either containing an insect repellent material (and, if desired, an aroma imparting liquid) or in the alternative being a hollow core wherein the insect repellent material (and, if desired, the aroma imparting material) is in the solid fused foamed polymeric particles which make up the core and wherein the void does not contain anything.

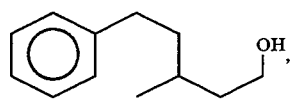

Figure 1:
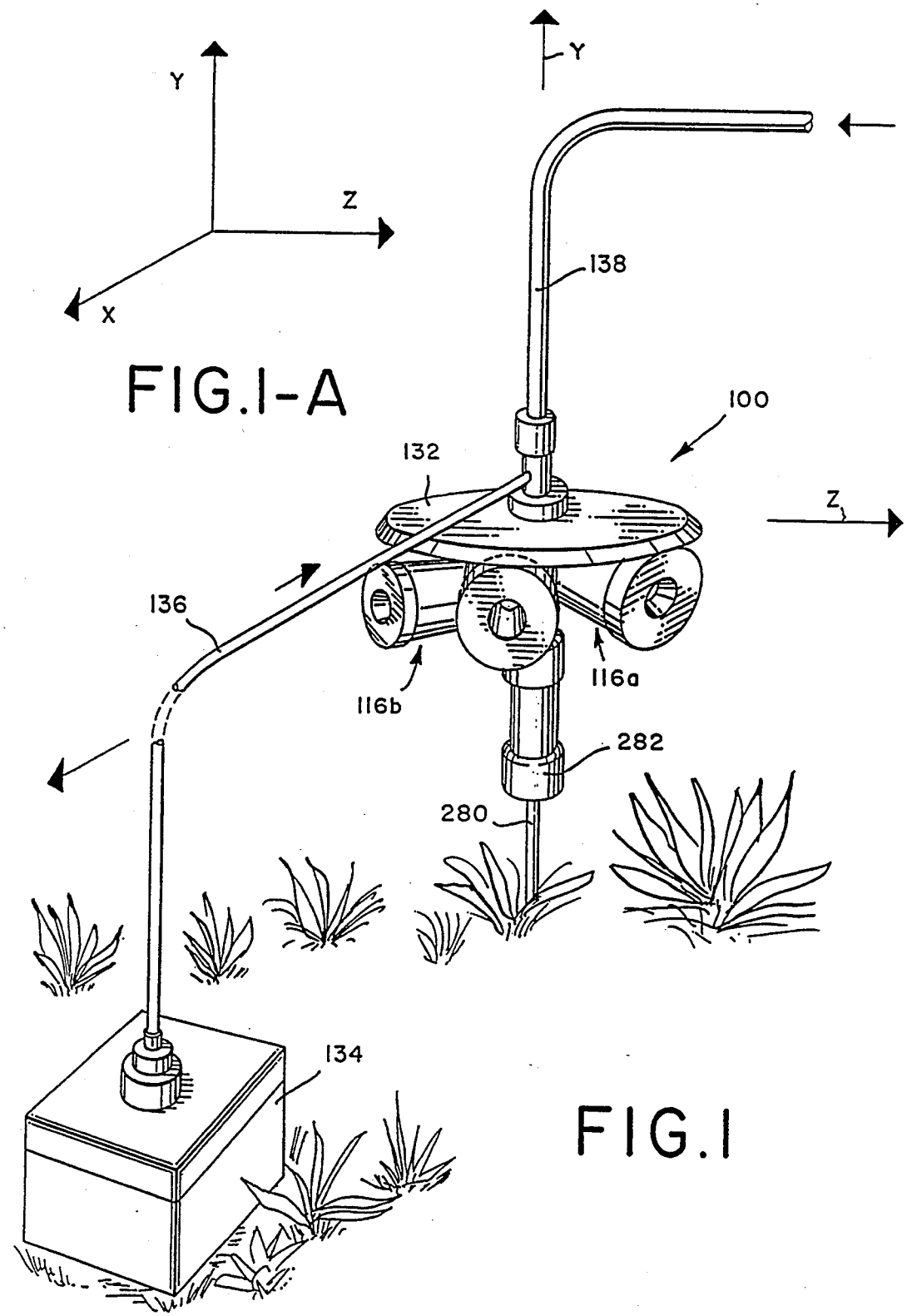
FIG. 1 is a perspective view of the semiochemical field trap for blood feeding arthropods of our invention.

the compound having the structure:

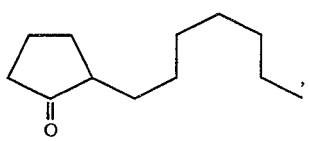

and the mixture of compounds having the structures:

and

FIG. 36(A) is a series of graphs depicting in three dimensions (in a rectangular mode for the "x" and "y" axes) showing the relative repellency of air, the compound having the structure:

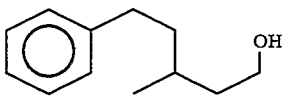

and the mixture of compounds having the structures:

and

The graphs are based on experiments run for a total of one hour with six intervals of ten minutes each. The results are tabulated in Table III(A), infra This series of graphs is for the attractiveness or repellency as against mosquitoes (Aedes aegypti).

FIG. 36(B) is a series of graphs depicted in three dimensions (in a rectangular mode for the "x" and "y"

axes) showing the relative repellency of air, the compound having the structure:

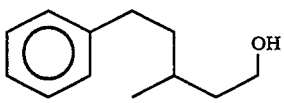

and the mixture of compounds having the structures:

and

The graphs are based on experiments run for a total of six hours with six intervals of one hour each. The results are tabulated in Table III(B), infra. This series of graphs is for the attractiveness or repellency as against mosquitoes (*Aedes aegypti*).

FIG. 37(A) is a series of graphs depicted in three dimensions (in a rectangular mode for the "x" and "y" axes) showing the relative repellency of air, the compound having the structure:

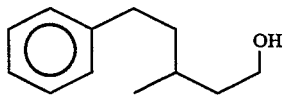

the compound having the structure:

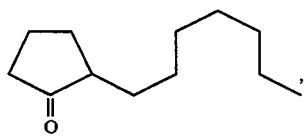

and the mixture of compounds having the structures:

and

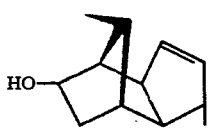

-continued

The graphs are based on experiments run for a total of one hour with six intervals of ten minutes each. The results are tabulated in Table IV(A), infra. This series of graphs is for the attractiveness or repellency as against mosquitoes (*Aedes aegypti*).

FIG. 37(B) is a series of graphs depicted in three dimensions (in a rectangular mode for the "x" and "y" axes) showing the relative repellency of air, the compound having the structure:

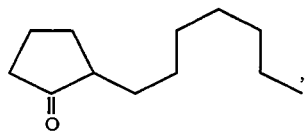

the compound having the structure:

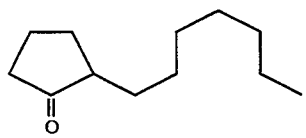

and the mixture of compounds having the structures:

and

The graphs are based on experiments run for a total of six hours with six intervals of one hour each. The results are tabulated in Table IV(B), infra. This series of graphs is for the attractiveness or repellency as against mosquitoes (*Aedes aegypti*).

FIG. 38(A) is a series of graphs depicted in three dimensions (in a rectangular mode for the "x" and "y" axes) showing the relative repellency of air and the compound having the structure:

of our invention. The graphs are based on experiments run for a total of one hour with six intervals of ten minutes each. The results are tabulated in Table V(A), infra. This series of graphs is for the attractiveness or repellency as against mosquitoes (*Aedes aegypti*).

FIG. 38(B) is a series of graphs depicted in three dimensions (in a rectangular mode for the "x" and "y" axes) showing the relative repellency of air and the compound having the structure:

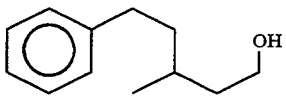

of our invention. The graphs are based on experiments run for a total of twelve hours with six intervals of two hours each. The results are tabulated in Table V(B), infra. This series of graphs is for the attractiveness or repellency as against mosquitoes (*Aedes aegypti*).

DETAILED DESCRIPTION OF THE DRAWINGS

Referring to FIGS. 1–12 and 17–24, the semiochemical field trap 100 for blood feeding arthropods is located in a three-space (as shown in FIG. 1A) defined by a vertical "y" axis and horizontal "x" and "z" axes each of which "x" and "z" axis is perpendicular to said "y" axis and each of which "x" and "z" axis is perpendicular to one another. The semiochemical field trap 100 is shown in perspective view in FIG. 1, standing in a field on stand 280 held in cup 282.

Referring to the embodiment of the semiochemical field trap for blood feeding arthropods illustrated in FIGS. 2, 3, 4, 4A, 5, 5A and 6 of prior application Ser. No. 887,138 filed on May 22, 1992, now U.S. Pat. No. 5,228,233 such a field trap comprises:

(1) an upright vertically disposed first hollow outer housing 102 having a vertical axis parallel to and on the "y" axis, having substantially rigid arthropod-impermeable vertically disposed side walls 104 encompassing and defining a first inner void 106 surrounded by said side walls and surrounding said "y" axis, said housing
  (A) having a side wall upper terminal end (with circumference 144) located in a first "x-z" plane perpendicular to said "y" axis;
  (B) having an upper arthropod-impermeable horizontal surface located in said first "x-z" plane being entirely contiguous with said side wall upper terminal end (having circumference 144) said upper horizontal surface (i) being substantially perpendicular to the vertical "y" axis of said hollow outer housing 102 and (ii) having an upper horizontal surface vertically-directed aperture therethrough 108;
  (c) having an upper circumferentially disposed outer housing section having outer surface area $A_{uo}$;

a middle circumferentially disposed outer housing section having outer surface area $A_{mo}$;

and a lower circumferentially disposed outer housing section having outer surface area $A_{lo}$ with the overall surface area of the outer housing $A_o$ being related to the other surface areas, thusly:

$A_o = A_{lo} + A_{mo} + A_{uo}$ with the overall surface area being indicated by reference numeral 142; the lower end of said upper outer housing section having a circumferential boundary $B_1$ with the upper end of said middle outer housing section; and the lower end of said middle outer housing section having a circumferential boundary $B_2$ with the upper end of said lower outer housing section;

(C) said upper outer housing section having a first horizontally arranged set $S_1$ of apertures 110a and 110b therethrough and a second horizontally arranged set $S_2$ of apertures 112a and 112b therethrough, each of the apertures of set $S_1$ being located along a vertical directional vector $\vec{V}_{si}$;

parallel to the "y" axis, each of the apertures of set $S_2$ being located along said vertical directional vector $\vec{V}_{si}$;

thereby enabling an aperture of set $S_1$ to correspond with an aperture of set. $S_2$ (for example, aperture 110a and aperture 112b) forming a corresponding aperture pair $PP_{s:1-2}$ with each of said apertures being located along the same vertically disposed directional vector $\vec{V}_{si}$, each aperture in said first aperture set $S_1$, 110a and 110b being located along a directional vector $\vec{V}_1$ in a second "x-z" plane with said directional vector $\vec{V}_1$ being perpendicular to said "y" axis and said vertically-disposed side walls 104 with $\vec{V}_1 \perp \vec{V}_{2i}$ and each aperture in said second aperture set $S_2$ 112a and 112b being located in a directional vector $$\vec{V}_2$$

being perpendicular to said "y" axis and said vertically-disposed side walls, with $$\vec{V}_2 \perp \vec{V}_{si}$$

and $$\vec{V}_1 \| \vec{V}_2;$$

(E) said middle outer housing section having a third horizontally arranged set of apertures $S_3$ (indicated by reference numerals 114a and 114b) at a location below and proximate said boundary $B_1$, each aperture in said third aperture set $S_3$ being located along a directional vector $$\vec{V}_3$$

in a fourth "x-z" plane, said directional vector $$\vec{V}_3$$

being perpendicular to said "y" axis and said vertically disposed side walls 104;

(2) extending outwardly from said first hollow outer housing 102, a plurality of horizontally disposed hollow housings 116a and 116b, with each of said horizontally disposed hollow housings;

(A) having rigid arthropod (impermeable substantially horizontally disposed side wall 118a;

(B) encompassing and defining a second inner void 120a;

(C) having a central axis located along a directional vector $$\vec{V}_H,$$

wherein $$\vec{V}_H$$

is located in a fifth "x-z" plane with $$\vec{V}_H$$

being perpendicular to said "y" axis;

$$\vec{V}_H$$

being substantially parallel to vector $$\vec{V}_1;$$

$$\vec{V}_H$$

being substantially parallel to $$\vec{V}_2$$

and $$\vec{V}_2$$

being substantially perpendicular to $$\vec{V}_{si};$$

Figure 4:
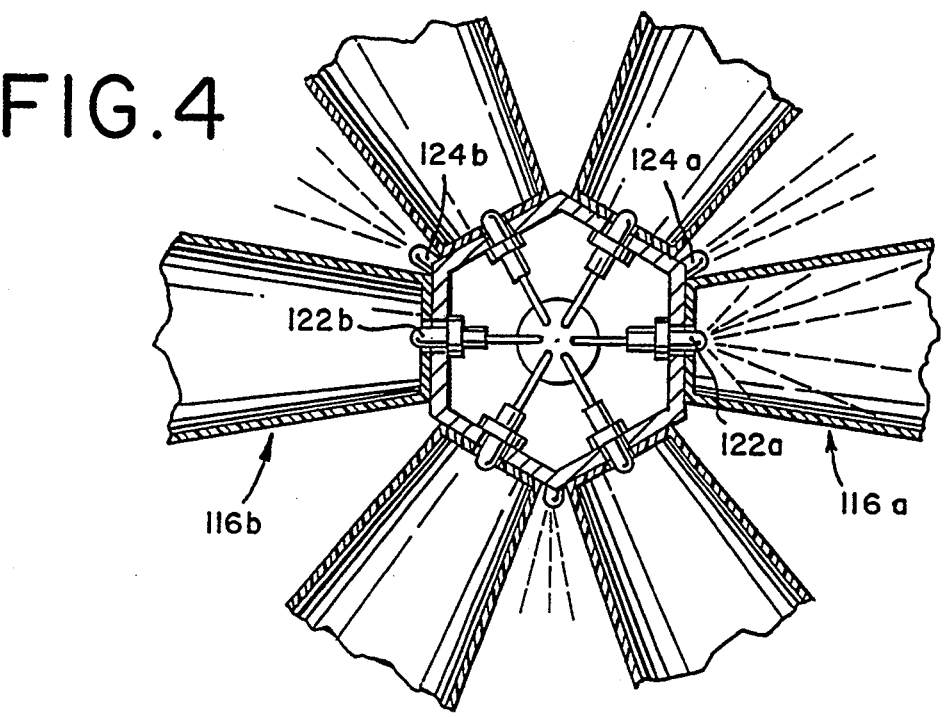
FIG. 4 is a top cut-away view of the apparatus of FIG. 2 taken along lines 4—4.
Figure 5:
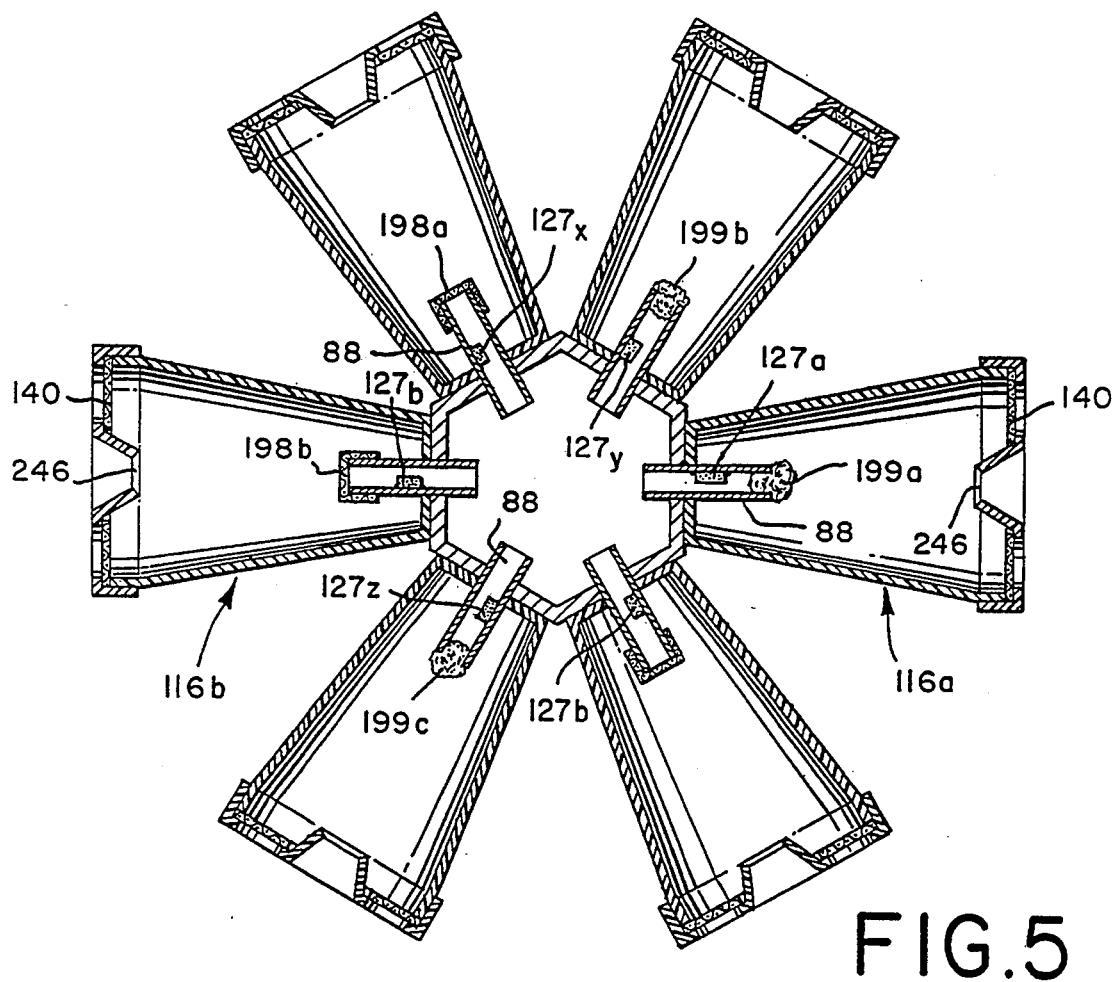
FIG. 5 is a cut-away top view of the apparatus of FIG. 2 taken along lines 5—5.

(D) having a circumferential substantially disposed outer terminal end located in a first "y-x/z" plane 190;

(E) having a circumferentially substantially vertically disposed inner terminal end 180 located in a second "y-x/z" plane, said inner terminal end 180 (i) being circumferentially and sealably contiguous with an outer surface area section 142 of said upper first outer housing section; and (ii) circumscribing an aperture pair $$PP_{s:1-2};$$

and (F) having located in said second inner void 120a a fixedly-positioned gas stream activatable semiochemical-containing matrix 126 comprising a porous containment agent containing in the interstices thereof at least one semiochemical sustainably releasable therefrom, with the matrix being supported by matrix support 128;

(4) one aperture of each of the aperture pairs $$PP_{s:1-2}$$

of aperture sets $S_1$ and $S_2$ containing a tightly sealably fitted radiation means 122a which effects transmission of insect attracting radiation to the interior of said horizontally disposed hollow housing 120a; the second aperture of each of the aperture pairs $$PP_{s:1-2}$$

of aperture sets $S_1$ and $S_2$ being capable of conveying a gas from the first inner void 106 of said first vertically disposed hollow outer housing 102 to the second inner void 120a of said horizontally disposed housing 116a and 116b in a direction whereby a substantial portion of the gas stream (coming through tubing 88 [in FIG. 5A]) impinges upon said semiochemical-containing matrix 126; however, the semiochemical matrix may be supported in the gas transmission tubing as shown in FIG. 5 where semiochemical matrix 127, 127a, 127x, 127y, 127z and 127b are supported in tubing. The tubing can have a screen on its outer orifice (in the inner void of the horizontally disposed hollow housing 120a), the screen being indicated by reference numerals 198a and 198b; or the orifice may be protected by means of cotton plug 199a, 199b and 199c (shown in FIG. 5). In the alternative the orifice of tube 88 may be protected from arthropods entering the inner void 106 using nylon mesh shown in use in FIG. 5A with the nylon mesh being indicated by reference numeral 98. Although shown to pierce the horizontally disposed hollow housing 116a and 116b, the radiation means 122a (e.g., light emitting diode) is preferably employed in back of the end surface plane 180 of horizontally disposed hollow housings 116a and 116b as shown in FIG. 4A with the inner end of horizontally disposed hollow housing 116a and 116b being indicated by reference numeral 96 in FIG. 4A.

(5) each of the apertures of said aperture set $S_3$ (114a and 114b) containing a tightly sealably-fitted radiation means (e.g., light emitting diode 122a) which transmits insect attracting radiation to a location in the immediate vicinity of said semiochemical field trap 100;

(6) at least one power supply means 130 (e.g., one or two batteries or a power supply means necessary to operate a laser diode shown by reference numeral 930 in FIG. 10B) associated with trap 100 energizing the radiation means 122a and 124a;

(7) air, 138 and/or carbon dioxide supply means 134, 136, for supplying air and/or carbon dioxide into said first inner void 106 via said vertically directed aperture 108 and then into said second inner void 120a via at least one of the apertures of aperture sets $S_1$ and $S_2$ (e.g., through tube 88, for example); whereby on engagement of the power supply means 130 with said radiation means 122a and 124a and operation of said air 138 and/or carbon dioxide supply means 134, 136, arthropods 160 in the vicinity of said trap are attracted by the activated radiation means 124a associated with aperture set $S_3$ and the gas emanating from said horizontally disposed hollow housings 116a to a location so close to said trap 100 that in the event that an attracting semiochemical in said matrix 126 is detected by at least one of said arthropods 160, said at least one of said arthropod 160 will enter the said inner void 120a of the horizontally disposed hollow housing 116a, 116b counter-current the gas stream emanating therefrom and remain permanently entrapped therein. The trapping means 140 facilitates trapping of the insects with the insects entering the horizontally disposed hollow housings 116a and 116b through orifice 246. Furthermore, carbon dioxide coming from carbon dioxide source 134 (e.g., dry ice held in a zippered bag) travels through line 136 and mixes with air 138 at mixing center 140. Optionally, trap 100 shown in FIG. 3 and in FIG. 2 may have a circular substantially planar shading means 132 extending substantially in the first "x-z" plane outwardly from the immediate vicinity of the circumference 144 of the first side wall upper terminal end.

The radiation means 124a preferably are located at a location in a "x-z" plane intermediate the radiation means 122a as shown in FIG. 4.

Figure 2:
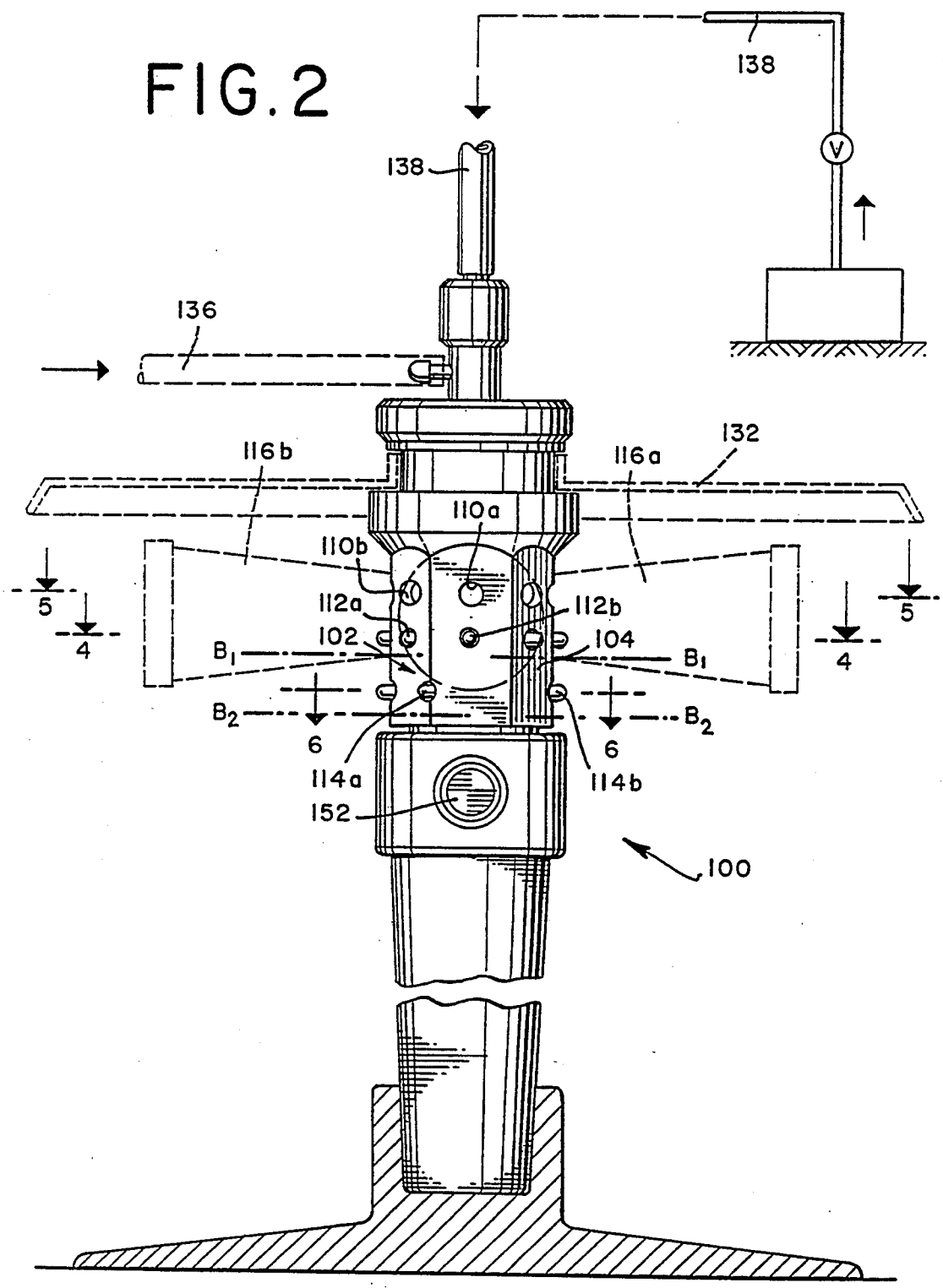
FIG. 2 is a side elevation view of the predecessor of one embodiment of the semiochemical field trap for blood feeding arthropods of our invention (covered in parent application, Ser. No. 887,138 filed on May 22, 1992 now U.S. Pat. No. 5,228,233).
Figure 3:
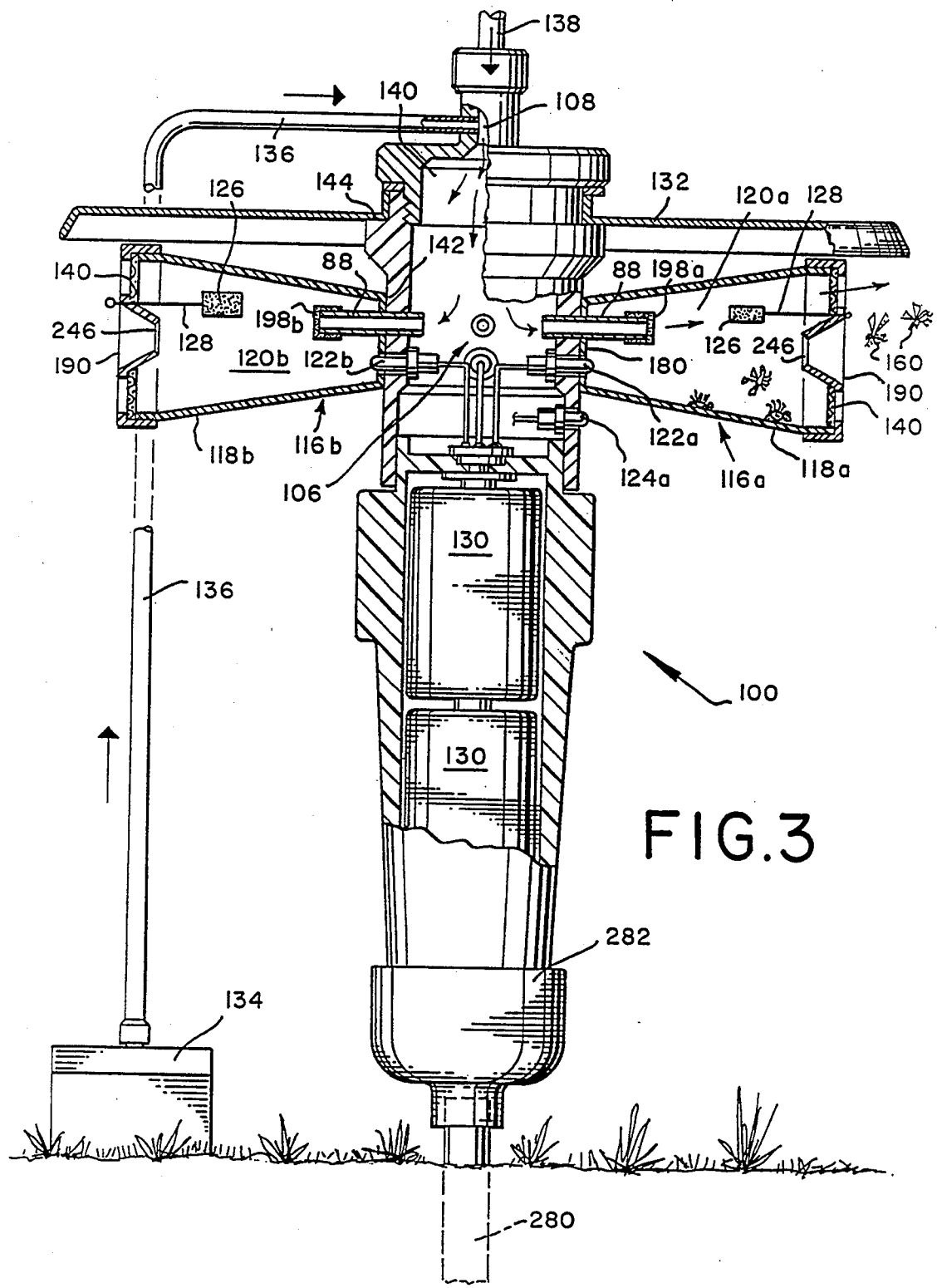
FIG. 3 is a cut-away side elevation view of the embodiment of the semiochemical field trap of FIG. 2.
Figure 10:
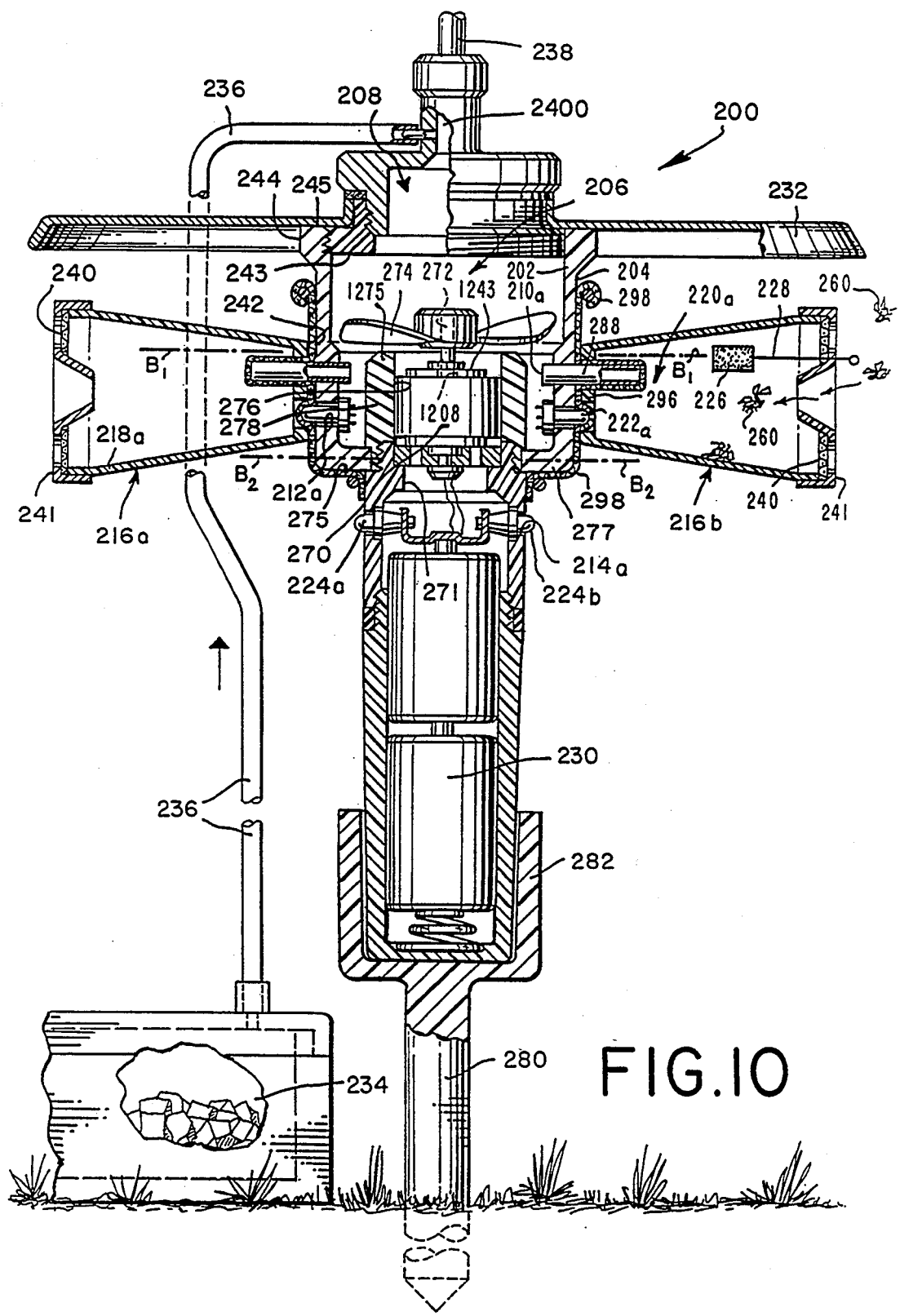
FIG. 10 is a cut-away side elevation view of a predecessor of a second embodiment of the semiochemical field trap for blood feeding arthropods of our invention (covered in Parent Application, Ser. No. 887,138 filed on May 22, 1992 now U.S. Pat. No. 5,228,233).

As shown in FIG. 8, the trapping means can be a sticky trapping means 140A located in plane 190 of the horizontally disposed hollow housings 116a and 116b in FIGS. 2 and 3 or the horizontally disposed hollow housings 216a and 216b in FIG. 10. The horizontally disposed hollow housings may have a screen 148 surrounding orifice 146 as shown in detail in FIG. 9. Circuitry for the light emitting diode radiation means 122a and 124a shown in FIG. 3 is shown in FIG. 7 wherein the power supply means is shown by reference numeral 130a and the switch to engage the power supply means is shown by reference numeral 152a. The light emitting diodes 122a, 122b and the like are shown by reference numerals 12a, 12b, 12c (for the LED) and 13a, 13b and 13c (for resistors associated with said LED's). The light emitting diode circuitry for LED 124a of set $S_3$ is shown by reference numerals 14a, 14b and 14c for the LED's and reference numerals 15a, 15b and 15c for resistors associated with said LED's.

With regard to the present invention which is an improvement on the aforementioned embodiment, radiation pulsating means (e.g., such as that illustrated in FIGS. 22 and 24) are associated with the apparatus of FIGS. 2, 3, 4, 4A, 5, 5A and 6.

Hence, additional radiation means can be located within said vertically disposed inner void 106 for conveying insect attracting radiation through substantially each of said gas transmission apertures of aperture set $S_1$ (110a and 110b) and/or aperture set $S_2$ (112a and 112b).

Figure 22:
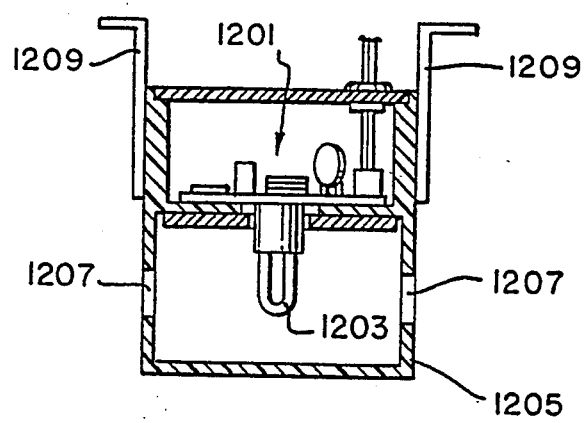
FIG. 22 is a cut-away side elevation view in detail of the radiation pulsating means radiation source used in the apparatus of FIG. 18.
Figure 24:
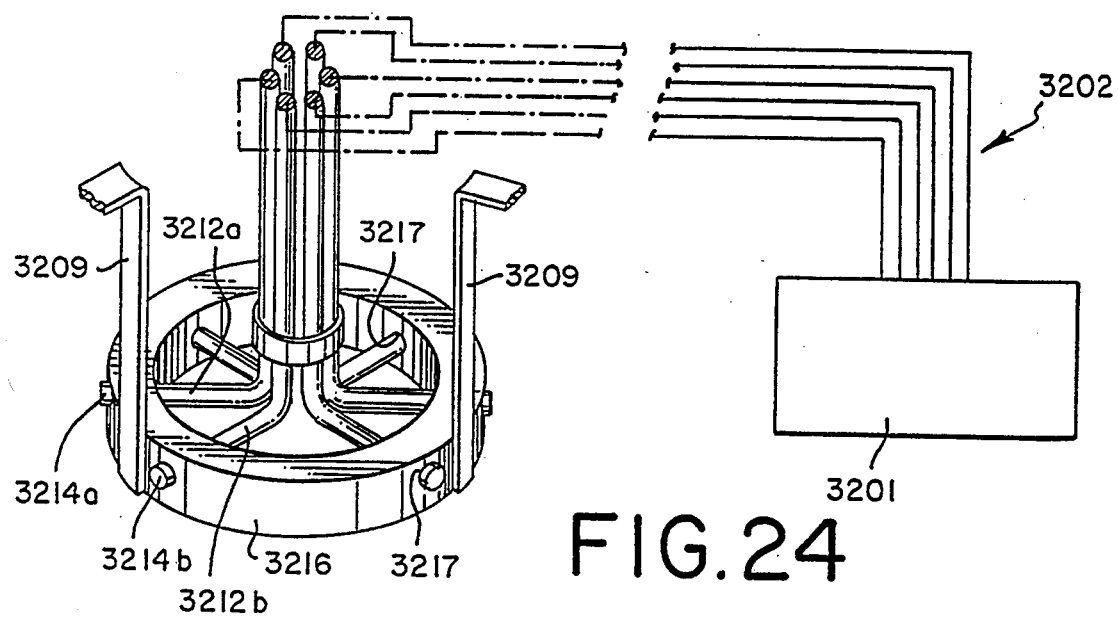
FIG. 24 is a schematic diagram showing in perspective the radiation source powered by radiation pulsating means for use in the apparatus of FIG. 19 taken together with the radiation pulsating means located externally from the apparatus of our invention.

Furthermore, radiation pulsing means shown in FIGS. 22 or 24 is connected to any or all of the radiation means causing the insect attracting radiation to have a frequency mimicking insect wing beat and/or insect visual sensing frequencies. Thus, referring to FIG. 3, radiation pulsating means of FIG. 22 can be located in inner void 106 emitting pulsating radiation through tubes 88 into voids 120a and 120b. Thus, strobelight unit 1205 being held by holder 1209 contains strobelight tube 1203 connected via electronic components 1201 to power source 130. The strobelight tube 1203 emits pulsating radiation through holes 1207 and then through tube 88.

FIG. 10 sets forth a second embodiment of the semiochemical field trap 200 for blood feeding arthropods of prior application Ser. No. 887,138 filed on May 22, 1992 which is located in a 3-space defined by a vertical "y" axis and horizontal "x" and "z" axes each of which "x" and "z" axis is perpendicular to said "y" axis and each of which "x" and "z" axis is perpendicu _ to one another (with the axes shown in FIG. 1A) comprising:

(1) a first upright vertically-disposed hollow outer housing 202 having a vertical central axis parallel to and/or on said "y" axis, having an outer surface area $A_o$ having substantially rigid arthropod-impermeable first vertically disposed side walls 204 encompassing and defining a first inner void 206, said housing:

(A) having a first side wall upper terminal end (having circumferential upper edge 244) located in a first "x-z" plane perpendicular to said "y" axis and a first side wall lower terminal end 275 located in a second "x-z" plane perpendicular to said "y" axis oppositely juxaposed with respect to said first side wall upper terminal end 245;

(B) having a first upper arthropod-impermeable horizontal surface 243 located in said first "x-z" plane and being entirely contiguous with said upper first side wall terminal end 245; said upper horizontal surface 243 (i) being substantially perpendicular to the vertical "y" axis of said hollow outer housing 202 and (ii) having a first upper horizontal surface vertically directed aperture 208 of effective diameter $D_u$ therethrough;

(C) having a lower arthropod impermeable horizontal surface 277 located in said second "x-z" plane and being entirely contiguous with said first side wall lower terminal end 275, said lower horizontal surface (i) being substantially perpendicular to the vertical axis of said first hollow outer housing 202 and (ii) having a lower horizontal surface vertically disposed aperture 271 of effective diameter $D_l$ therethrough wherein $D_l$ is substantially greater than $D_u$;

(D) having an upper circumferentially disposed first outer housing section having outer surface area $A_{uo}$ and a lower circumferentially disposed first outer housing section having outer surface area $A_{lo}$ with $A_o = A_{lo} + A_{uo}$ said lower first outer housing section having a first horizontally arranged set $S_1$ of apertures 210a therethrough and a second horizontally arranged set $S_2$ of apertures 212a therethrough, each of the apertures of said set $S_1$ being located along a vertical directional vector $\vec{V}_{si}$ parallel to the "y" axis and each of the apertures of set $S_2$ being located along said vertical directional vector $\vec{V}_{sj}$ parallel to the "y" axis thereby enabling an aperture 210a of aperture set $S_1$ to correspond with an aperture 212a of aperture set $S_2$ forming a corresponding aperture pair $PP_{s;1-2}$ with each of the apertures 210a and 212a being located along the same vertically disposed directional vector $\vec{V}_{si}$ , each aperture in said first set $S_1$ being located along the horizontally disposed directional vector $\vec{V}_1$ being perpendicular to said "y" axis and said vertically disposed side walls; with $\vec{V}_1 \perp \vec{V}_{si}$ and each aperture 212a in said second aperture set $S_2$ being located in a directional vector $\vec{V}_2$ in a fourth "x-z" plane, said directional vector $\vec{V}_2$ being perpendicular to said "y" axis and said vertically disposed side walls 204, with $\vec{V}_2 \perp \vec{V}_{2i}$ , the lower end of said upper outer housing section being the upper end of said lower outer housing section at a boundary $B_1$ located in a fifth "x-z" plane parallel to said first, second, third and fourth "x-z" plane;

(2) a second upright vertically disposed hollow inner housing 276 substantially coaxial with said first hollow outer housing 202 said inner housing 276 being partially circumscribed by said outer housing 202;

(A) having an upper circumferentially disposed outer section having area $A_{iu}$ located within said outer housing 202; a middle circumferentially disposed outer housing section having area $A_{im}$ located immediately below the lower end of said outer housing, and a lower circumferentially disposed section having area $A_{il}$ located immediately below said middle section with $A_i = A_{iu} + A_{il} + A_{im}$, the lateral boundary between said upper section and said middle section being located at boundary $B_2$ in said second "x-z" plane, said lateral boundary $B_2$ being coplanar with and parallel to said first side wall lower terminal end 275;

(B) having rigid arthropod-impermeable second vertically disposed side walls 278;

(C) having a second side wall upper terminal end 1275 located in said fifth "x-z" plane substantially coplanar with said boundary $B_1$;

(D) having a second upper arthropod-impermeable horizontal surface 1243 located in said fifth "x-z" plane and being entirely contiguous with said second side wall upper terminal end 1275, substantially coplanar with said boundary $B_1$, said second upper horizontal surface 1243 being a finite distance $D_{1-2}$ below said first upper horizontal surface 243, said second upper horizontal surface 1243 having a vertically directed aperture 1208 therethrough substantially coaxial with the vertical "y" axis of said second hollow inner housing 276; and (E) having a third horizontally arranged set of apertures $S_3$ (indicated by reference numeral 214a) at a location below and proximate said boundary B₂, each aperture 214a in said third set S₃ being located along a directional vector $$\vec{V}_3$$

in a sixth "x-z" plane, said directional vector $$\vec{V}_3$$

being perpendicular to said "y" axis and said vertically disposed side walls 278;

(F) the outer surface of said inner housing being sealably fitted at boundary B₂ within and circumferentially contiguous with the inner circumferential edge of the lower horizontal surface vertically disposed aperture 271 of said hollow outer housing 202;

(3) extending outwardly from said first hollow outer housing 202, a plurality of horizontally disposed hollow housings 216a and 216b, with each of said horizontally disposed hollow housings 216a and 216b;

(A) having rigid arthropod (impermeable horizontally disposed side walls 218a;

(B) encompassing and defining a second inner void 220a;

(C) having a central axis located along a directional vector $$\vec{V}_H$$

wherein $$\vec{V}_H$$

is located in a seventh "x-z" plane with $$\vec{V}_H$$

being perpendicular to said "y" axis;

$$\vec{V}_H$$

being substantially parallel to vector $$\vec{V}_1$$

$$\vec{V}_H$$

being substantially parallel to $$\vec{V}_2;$$

and $$\vec{V}_H$$

being substantially perpendicular to $$\vec{V}_{s_i};$$

(D) having a circumferential substantially vertically disposed outer terminal end 241 located in a first "y-x/z" plane;

(E) having a circumferential substantially vertically disposed inner terminal end 296 oppositely juxtaposed to said vertically disposed outer terminal end 241 located in a second "y-x/z" plane, said inner terminal end 296 (i) being sealably contiguous with an outer surface section 242 of said lower first outer housing section 202 and (ii) circumscribing an aperture pair $$PP_{s:1-2}$$

(indicated by reference numerals 210a and 212a;

(F) having located in said second inner void 220a a fixedly-positioned gas stream-activatable semiochemical-containing matrix 226 comprising a porous containment agent containing in the interstices thereof at least one semiochemical sustainably releasable therefrom (with the matrix being supported by matrix support 220 extending from outer terminal end 241; and (G) having arthropod 260 entrapment means 240 (e.g., a sticky substance) located substantially within said second inner void 220a;

(4) one aperture 210a or 212a of each of the aperture pairs $$PP_{s:1-2}$$

of aperture sets S₁ and S₂ containing a tightly sealably fitted radiation means 222a (e.g., a light emitting diode or a laser diode) which effects transmission of insect-attracting radiation to the interior 220a of said horizontally disposed hollow housing 216a, 216b; the second aperture of each of the aperture pairs $$PP_{s:1-2}$$

of aperture sets S₁ and S₂ being capable of conveying a gas (e.g., through tube 288 protectively screened by nylon mesh 298) of said first vertically disposed hollow outer housing 202 to the second inner void 220a of said horizontally disposed outer housing 216a, 216b, in a direction whereby a substantial portion of the gas stream impinges upon said semiochemical containing matrix 226;

(5) each of the apertures of said aperture set S₃ (indicated by reference numeral 214a) containing a tightly sealably fitted radiation means 224a (e.g., a light emitting diode which may be blue light, green light or infra-red radiation) which transmits insect attracting radiation to a location in the immediate vicinity of said semiochemical field trap 200;

(6) a substantially vertically disposed drive shaft 272 coaxial with said "y" axis supported for rotary motion about its axis, extending from within said second upright vertically disposed hollow inner housing below the bottom at boundary B₂ of said upright vertically disposed hollow outer housing 202, through said vertically directed aperture 1208 of said second upper horizontal surface 1243 of said second upright vertically disposed hollow inner housing 276, into said first inner void 206 of said first upright hollow outer housing 202, along the longitudinal dimension of said second upright hollow inner housing 276 and along the longitudinal dimension of said first upright hollow outer housing 202;

(7) motor means 270 connected to a first lower end of said drive shaft 272 for rotating said drive shaft 272 about its axis;

(8) air flow creation means attached to a second upper end of said drive shaft (e.g., a propeller 274), being of such a design whereby the rotation of said drive shaft 272 directly causes the rotation of said air flow creation means 274 and induces the flow of air downwardly through said first upper horizontal surface vertically directed aperture 208 into and through said first inner void 206, and then through one aperture of each of said aperture pairs $PP_{s:1-2}$ of aperture sets $S_1$ and $S_2$ into and through each of said second inner voids 220a of each of said horizontally disposed hollow housings 216a, 216b; and (9) at least one power supply means (e.g., batteries 230) associated with said trap 200, energizing said radiation means 222a and 224a and said motor means 270;

whereby on engagement of the power supply means 230 with said motor means 270 and said radiation means 222a and 224a, arthropods 260 in the vicinity of said trap 200 are attracted by the radiation means associated with aperture set $S_3$, 224a and gas emanating from the outer terminal end 241 of said horizontally disposed hollow housings 216a, 216b to a location so close to said trap that in the event that an attracting semiochemical in said matrix 226 is detected by at least one of said arthropods 260, said at least one arthropod will enter said second inner void 220a of said horizontally disposed hollow inner housing 216a, 216b counter-current to the gas stream emanating therefrom and remain permanently entrapped therein, e.g., using trapping means 240. The carbon dioxide source can be solid dry ice enclosed in a zippered bag as indicated by reference numeral 234 and may be passed through line 236 mixing with air coming from air line 238 at mixing point 240. The mixture of air and $CO_2$ is then passed into the first inner vertically disposed hollow housing void 206.

With regard to the present invention which is an improvement on the aforementioned FIG. 10 embodiment, preferred embodiments of which are illustrated in FIGS. 17, 18, 19, 20, 21 and 23, radiation pulsating means (for example, as illustrated in FIGS. 22 and 24) are associated with such apparatus.

Hence, additional radiation means (2203 in FIG. 17; 1203 in FIG. 18; and 3201 and 3202 in FIG. 19) can be located within said vertically disposed inner void 206 for conveying insect attracting radiation through substantially each of said gas transmission apertures of aperture set $S_1$ and/or aperture set $S_2$.

Furthermore, radiation pulsing means shown in FIGS. 22 and 24 connected to one or more radiation means cause the insect attracting radiation to have a frequency mimicking insect wing beat frequencies and/or insect visual sensing frequencies.

Figure 17:
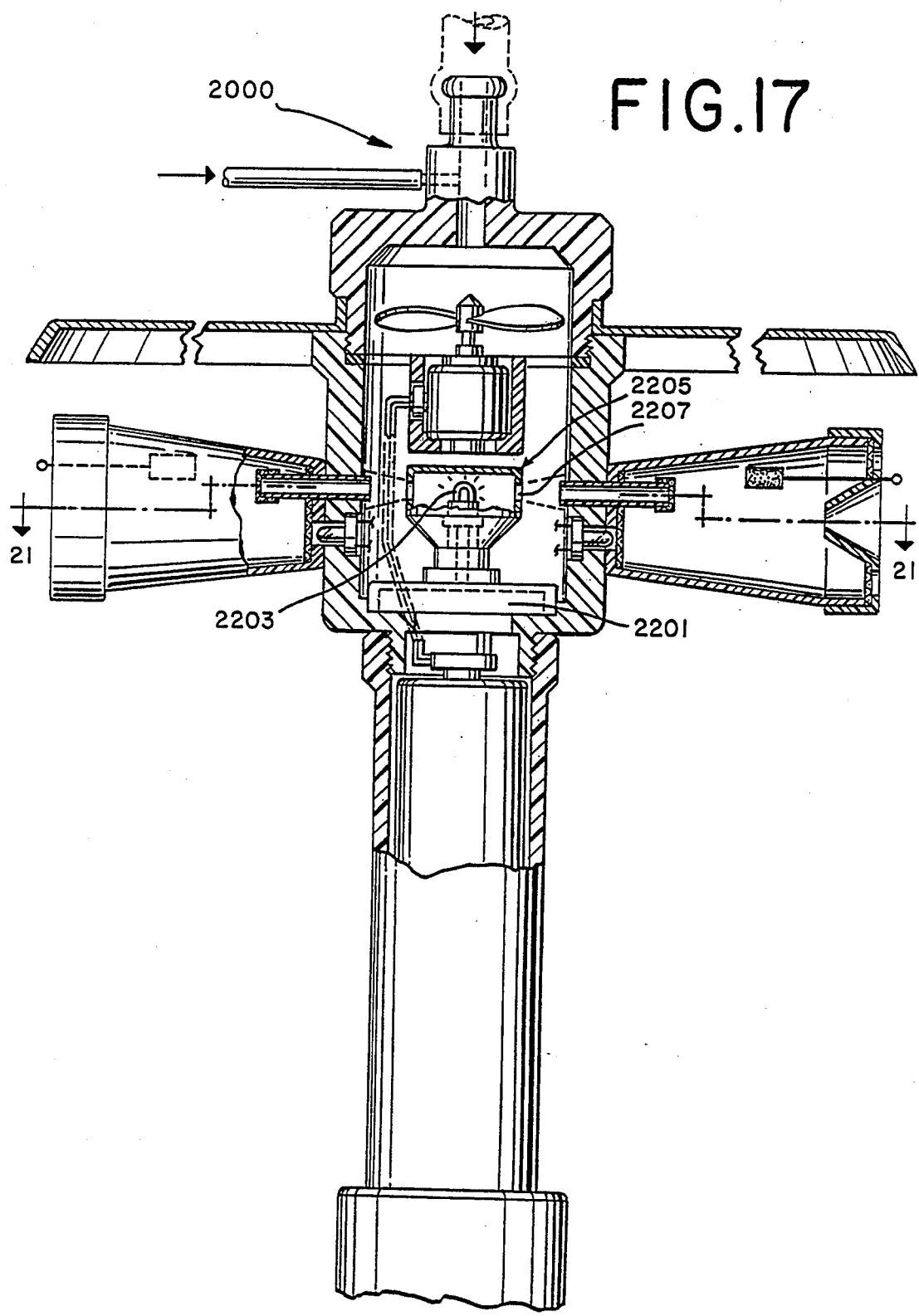
FIG. 17 is a side elevation view of one embodiment of the semiochemical field trap for blood feeding arthropods of our invention containing internally-located radiation pulsing means.

More specifically, strobelight tube 2203 is located in closed box unit 2205 in FIG. 17. The radiation therefrom is emitted through holes 2207 in the apparatus of FIG. 17 (referred to as unit 2000). The circuitry powering the strobelight tube is indicated by reference numeral 2201. FIG. 17 is also shown in detail by reference to FIG. 21, the top cut-away view of FIG. 17 taken along lines 21—21. Thus, the radiation emitted by strobelight tube 2203 through holes 2207 is emitted through tube 88 into the horizontally disposed hollow housing means 116a and 116b.

Figure 18:
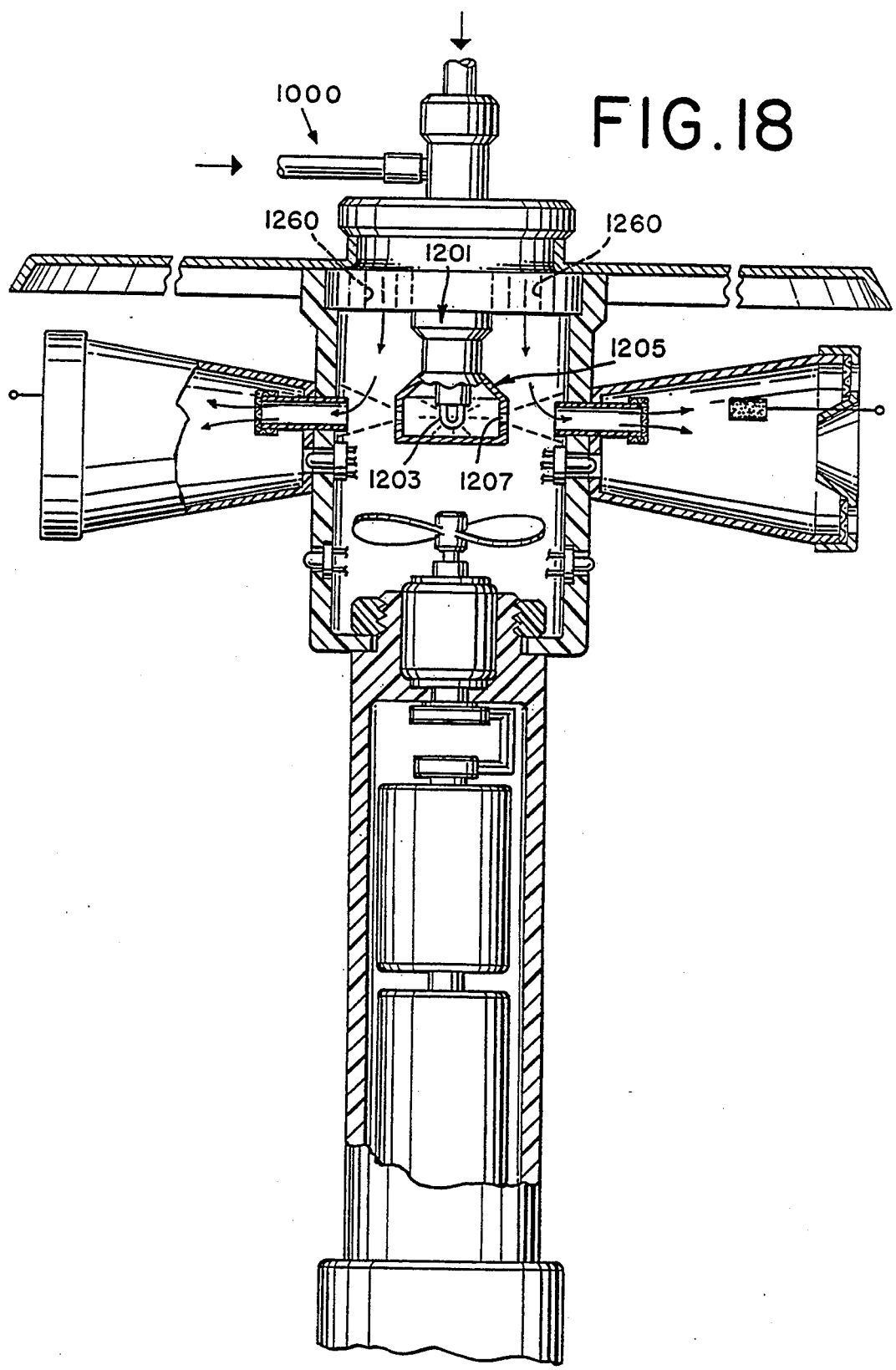
FIG. 18 is a side elevation view of a second embodiment of the semiochemical field trap for blood feeding arthropods of our invention containing internally-located radiation pulsing means.

Strobelight tube 1203 located in strobelight unit 1205 in the apparatus of FIG. 18 (indicated by reference numeral 1000) is shown in detail in FIG. 22. Strobelight tube 1203 emits pulsating radiation as a result of pulsating radiation power emitted via electronic components 1201. The said pulsating radiation from strobelight tube 1203 is emitted through holes 1207. The strobelight box 1205 is affixed to the ceiling of unit 1000 via holders 1209. Simultaneously with the emission of pulsating radiation from strobelight unit 1205, gas through gas passages 1260 is forced into the horizontally disposed hollow outer housings.

Figure 19:
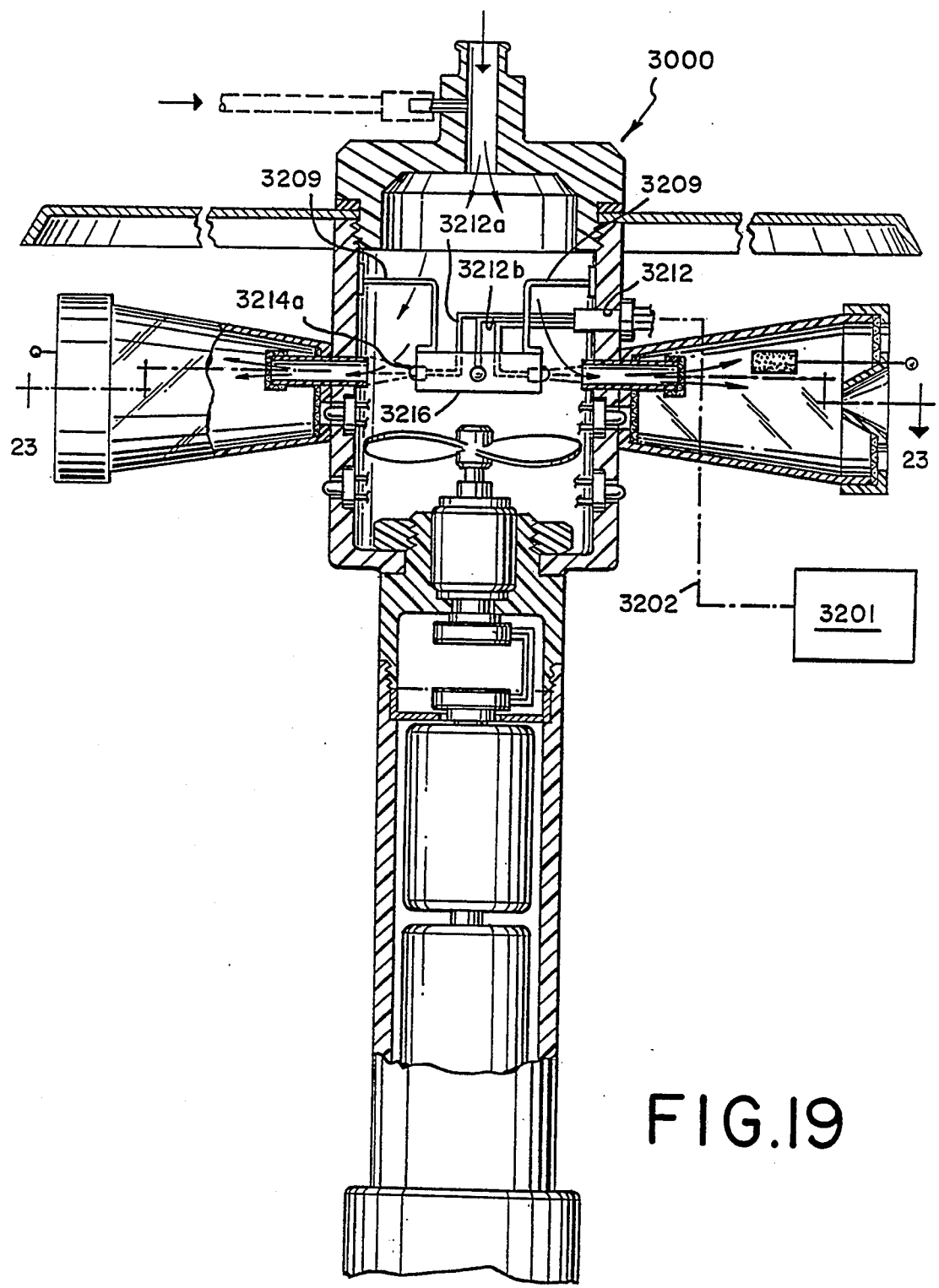
FIG. 19 is a side elevation view of a third embodiment of the semiochemical field trap for blood feeding arthropods of our invention containing externally-located radiation pulsing means.
Figure 23:
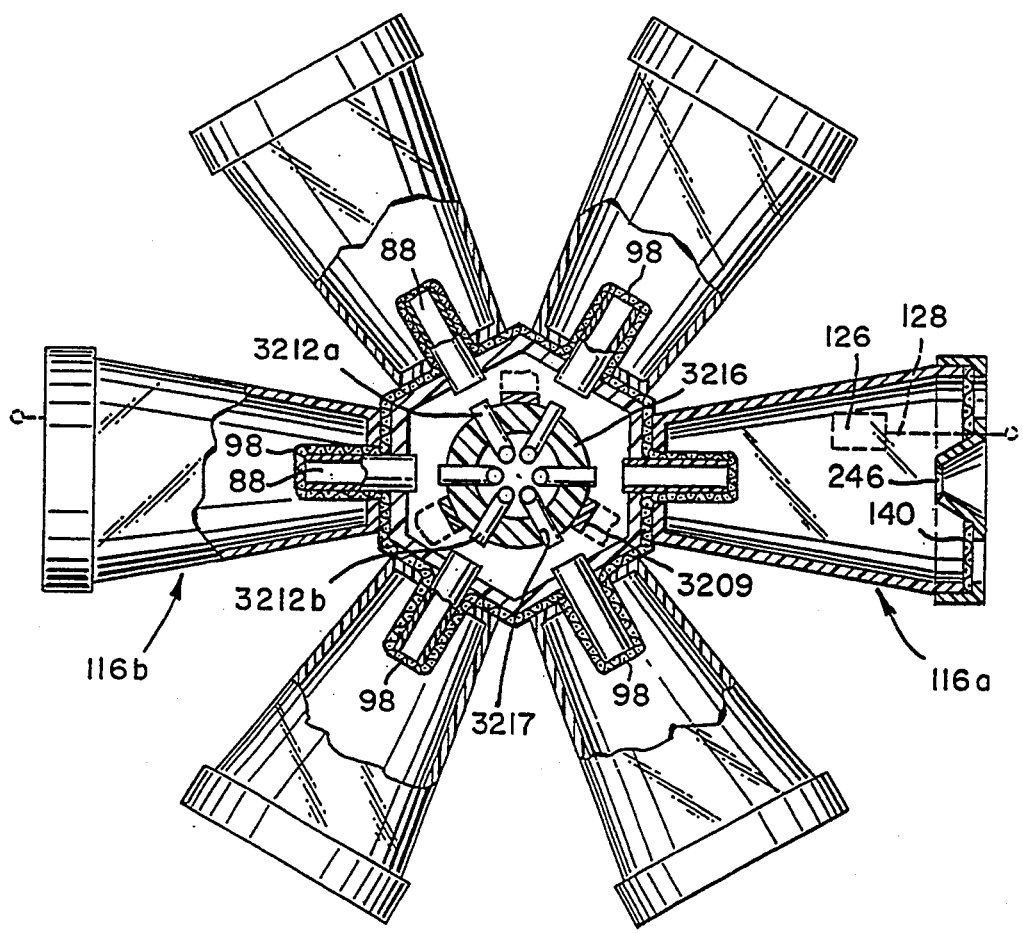
FIG. 23 is a top cut-away view of the apparatus of FIG. 19 taken along lines 23—23.

Referring to FIG. 19 which illustrates unit 3000, the strobelight power unit is external to the vertically disposed hollow void. Circuitry and strobelight (combined) 3201 emits radiation through fiber optic assembly 3202 through connection 3212 into suspended ring light assembly 3216 wherefrom as shown in FIG. 24, pulsating radiation is emitted through holes 3217 located in suspended ring 3216. The fiber optic strands are indicated by reference numerals 3212a and 3202 (on the outside of unit 3000). FIG. 23 is a cut-away top view of the apparatus of FIG. 19 looking in the direction of the arrows 23—23. Thus, the radiation emitted from 3214b and 3214a passes through tubes 88 into the horizontally disposed hollow housing voids 116a and 116b.

Figure 20:
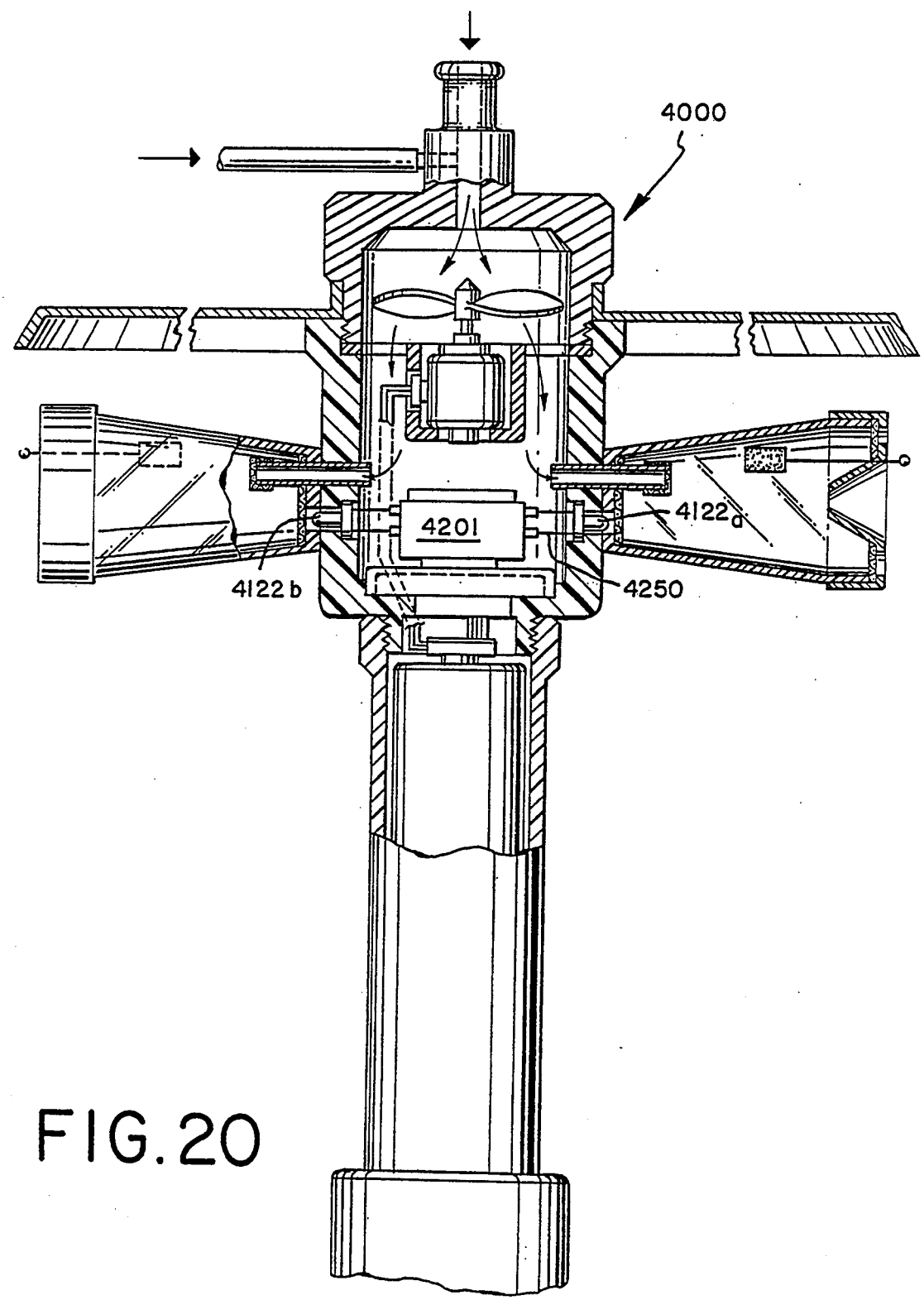
FIG. 20 is a side elevation view of a fourth embodiment of the semiochemical field trap for blood feeding arthropods of our invention containing internally-located radiation pulsing means.
Figure 21:
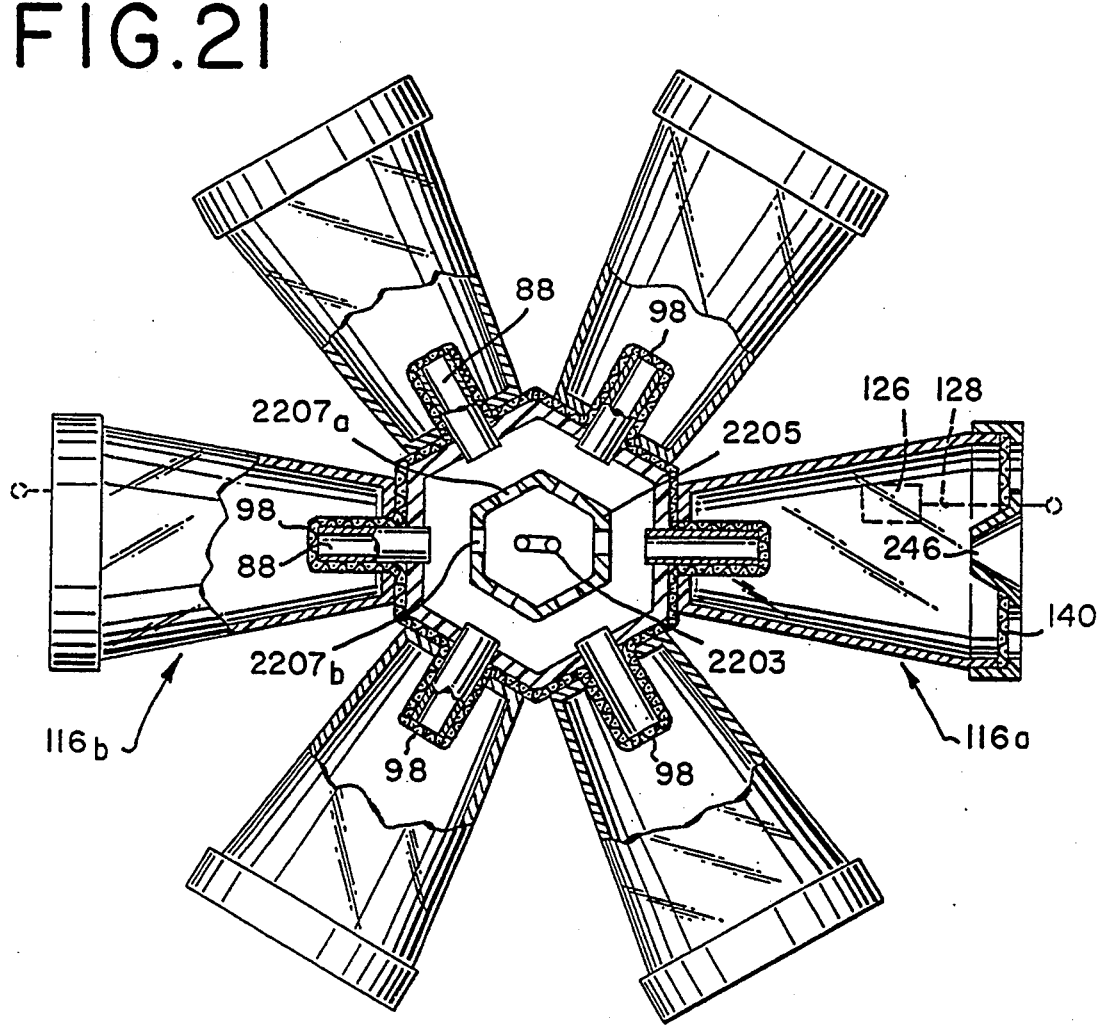
FIG. 21 is a top cut-away view of the apparatus of FIG. 17 taken along lines 21—21.

Referring to FIG. 20, (indicated by reference numeral 4000), diode bulbs 4122a and 4122b are connected via electronic circuitry 4201 through wires 4250 to radiation pulsing means. Thus, instead of using an actual "strobelight", the radiation pulsing means will cause radiation emitted from diodes 4122a and 4122b to pulse at specific frequencies between 50 and 400 Herz.

Optionally, trap 200 may have a circular substantially planar shading means 232 extending substantially in said first "x-z" plane outwardly from the immediate vicinity of the circumference 244 of said first side wall upper terminal end 245.

FIG. 10A sets forth in detail a cut-away side elevation view of a horizontally disposed hollow outer housing embodiment useful with the apparatus of our invention as embodied in FIGS. 2, 3 and 10. In FIG. 10A, gas emanating from tube 288 covered with mesh 298 impinges upon semiochemical containing matrix 226 which causes evolution of an attractant or a repellent. If an attractant is evolved, blood feeding arthropods 260 are attracted into the horizontally disposed housing. Radiation from LED 922a is emitted from behind inner surface 296 of the horizontally disposed hollow housing with the inner surface 296 being translucent so that the radiation is diffused from the entire surface 296 into the inner void of the hollow outer housing. Radiation from LED 222a is emitted to further attract arthropods 260 into the area of the trap.

FIG. 10B shows in detail another embodiment of the horizontally disposed hollow housing using instead of a LED a laser diode 922. Between the laser diode and the inner surface of the horizontally disposed hollow housing 997 is a diffusion lens 923 for the laser diode 922. The laser diode 922 is powered using power source 930 and laser circuitry 931. The laser diode preferably emits $CO_2$ wave length radiation, e.g., approximately 960 nanometers. Air evolved from tube 988 screened with nylon mesh screen 998 (to prevent arthropods from travelling through tube 988 from the inner void of the horizontally disposed housing impinges upon semiochemical-containing matrix 926. If a repellent is evolved from semiochemical matrix 926, then arthropods are trapped in the hollow outer housing, for example, on sticky surface 940a.

Figure 11:
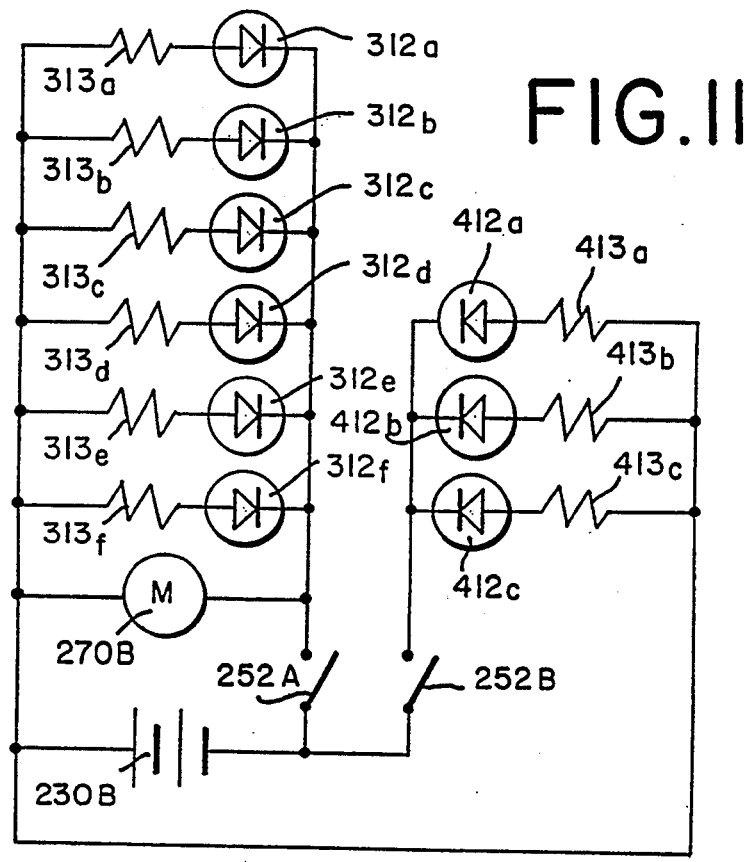
FIG. 11 is a diagram showing the circuitry useful in operating the apparatus of FIG. 10 using two separate switches; one for the radiation emission entering the horizontally disposed hollow housing means and the other for the radiation emission below the horizontally disposed hollow housing means.
Figure 12:
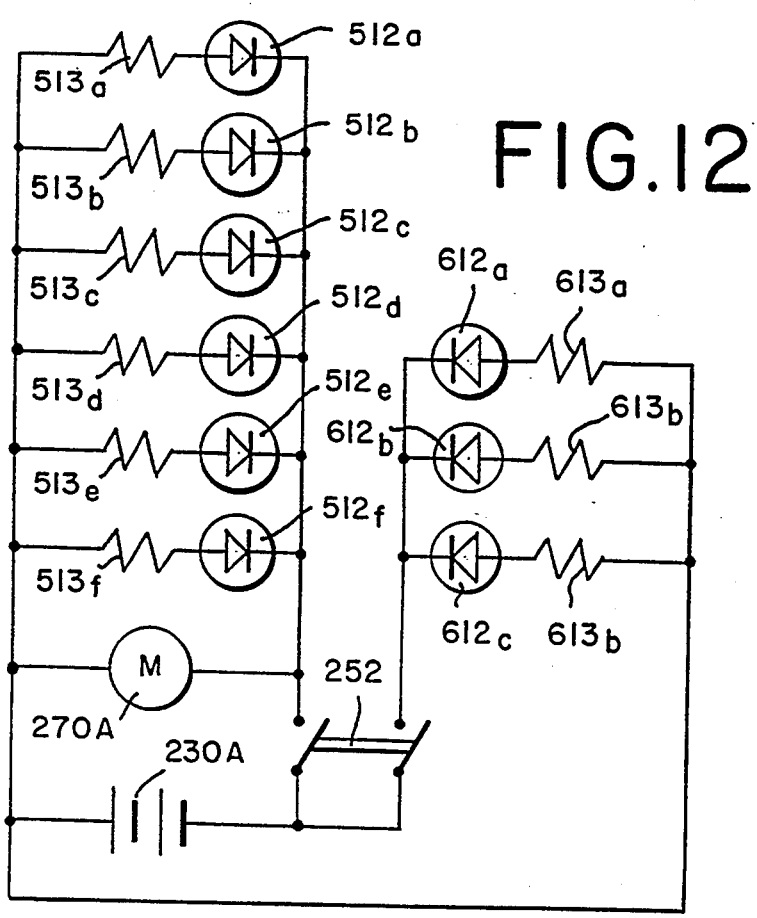
FIG. 12 is a schematic diagram of the circuitry for the apparatus of FIG. 10 using a single switch for the radiation means as well as for the motor means useful in said apparatus of FIG. 10.

FIGS. 11 and 12 set forth the circuitry for the motor means and radiation means circuits for the apparatus of the embodiment of FIG. 10. An embodiment shown in FIG. 11 shows the use of two separate switches; whereby, switch 252b will cause the engagement of power with diodes 412a, 412b and 412c associated with resistors 413a, 413b and 413c, respectively. Switching on switch 252a will activate motor means 270b as well as diodes 312a, 312b, 312c, 312d, 312e and 312f associated with resistors 313a, 313b, 313c, 313d, 313e and 313f.

The embodiment shown in FIG. 12 shows the use of one switch 252 which will activate diodes 612a, 612b and 612c associated with resistors 613a, 613b and 613c as well as diodes 512a, 512b, 512c, 512d, 512e and 512f associated with resistors 513a, 513b, 513c, 513d, 513e and 513f, respectively, along with motor means 270a using power supply source 230a. The power supply source in FIG. 11 is shown by reference numeral 230b.

The bar graph of FIG. 13 shows the employment of the apparatus of FIG. 10 in testing the attractancy or repellency of various materials. It is shown that the mixture of compounds having the structures:

and

repels mosquitoes as shown by a low mean of bar graph 803. This repellency is similar to the repellency effect on mosquitoes of bay leaf oil shown by bar graph 802. On the other hand bar graph 801 (for clean air) shows attractancy for mosquitoes as do bar graphs 804 (lavender oil) and 805 (vetiver oil).

Figure 14:
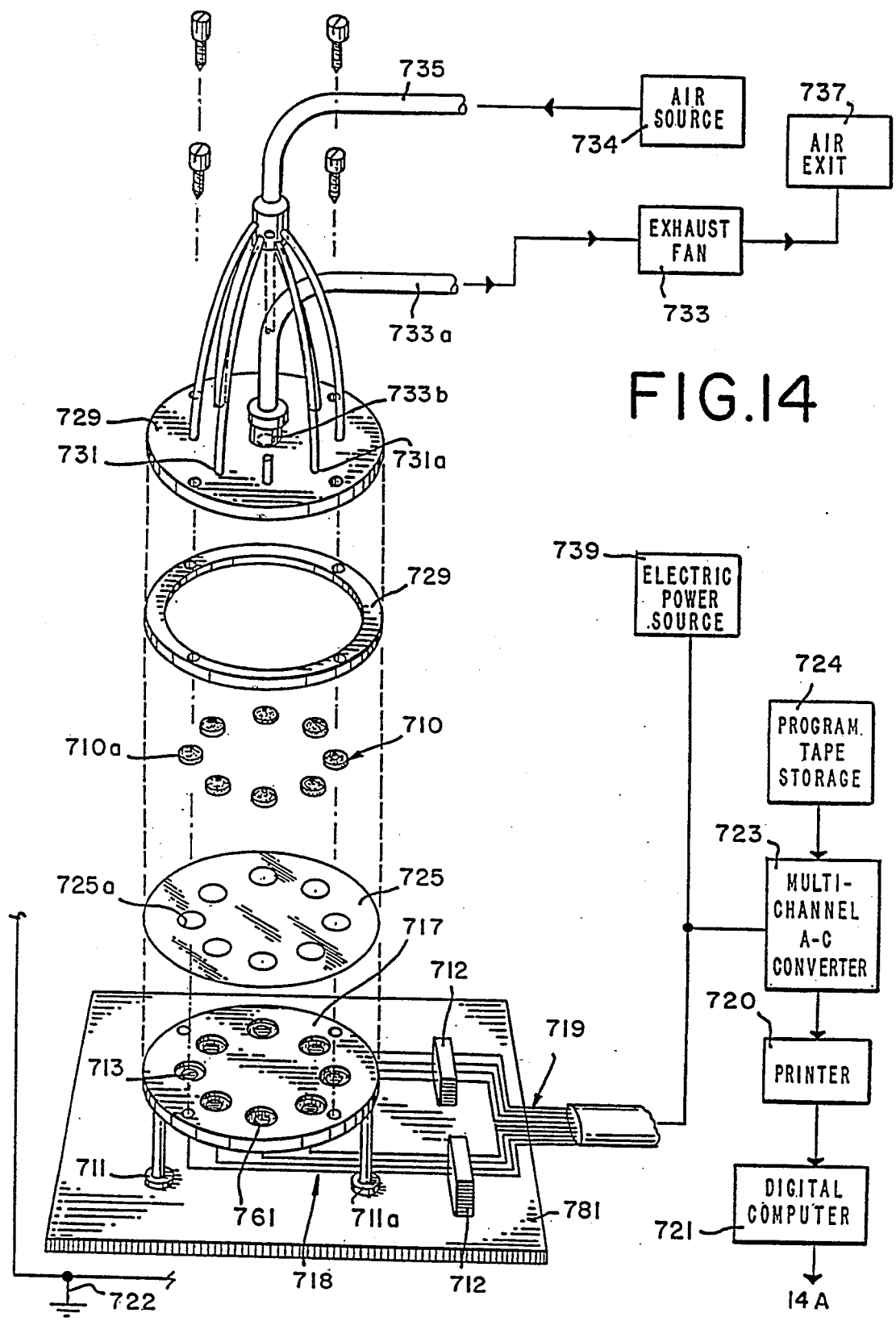
FIG. 14 is a schematic diagram (blown up for illustration purposes) of laboratory olfactometer apparatus useful in ascertaining the efficacy of the cycloalkanol derivative-containing composition of Parent Application, Ser. No. 887,138 filed on May 22, 1992 now U.S. Pat. No. 5,228,233 as a repellent for house flies (Musca domestica L.(Diptera:Muscidae)) and Aedes aegypti indicating in schematic block flow diagram form the utilization of computer assisted efficacy measuring apparatus.
Figure 15:
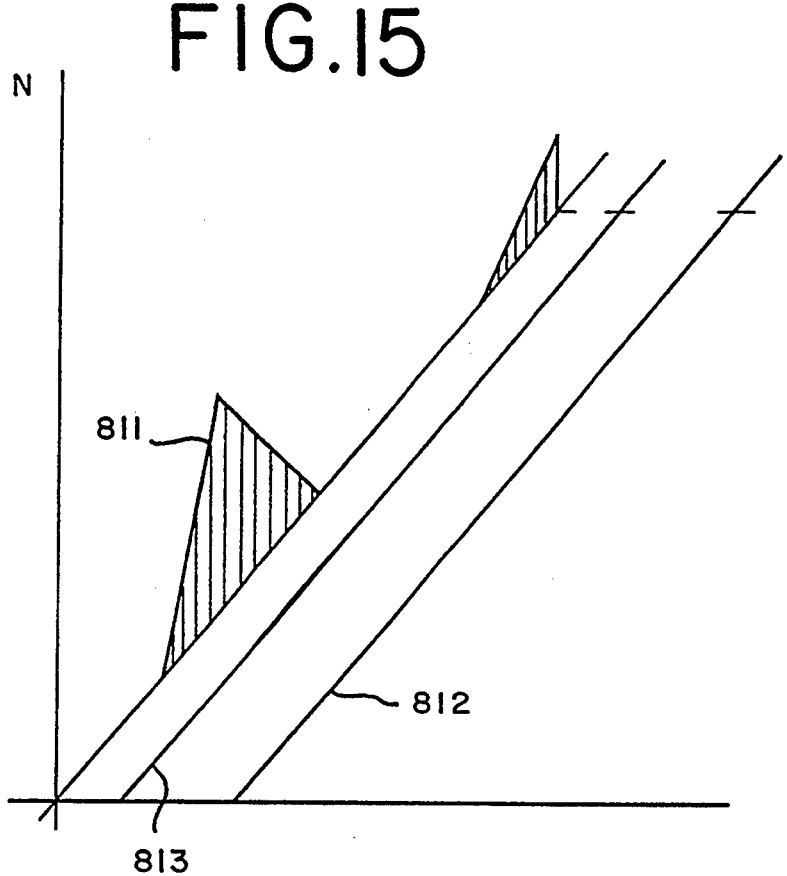
FIG. 15 is a series of graphs depicted in three dimensions (in a rectangular mode for the "x" and "y" axes) showing the relative repellency of air, bay leaf oil and the cycloalkanol derivative-containing composition of Parent Application, Ser. No. 887,138 filed on May 22, 1992 now U.S. Pat. No. 5,228,233. The graphs are based on experiments run for a total of one hour with six intervals of 10 minutes each. The results are tabulated in Table II, infra. This series of graphs is for the attractiveness or repellency as against house flies (Musca domestica L.(Diptera:Muscidae)).

The data shown in FIG. 13 is confirmed using a laboratory olfactometer of FIGS. 14 and 14A. This data is set forth in FIGS. 15 and 16. In FIG. 15, *Musca Domestica* L.(Diptera Muscidae) is shown to be attracted by clean air (the graph indicated by reference numeral 811) and is shown to be repelled by the mixture of compounds having the structures:

and

(shown by graph 813) and are shown to be repelled by bay leaf oil (as shown in the graph indicated by reference numeral 812).

Figure 16:
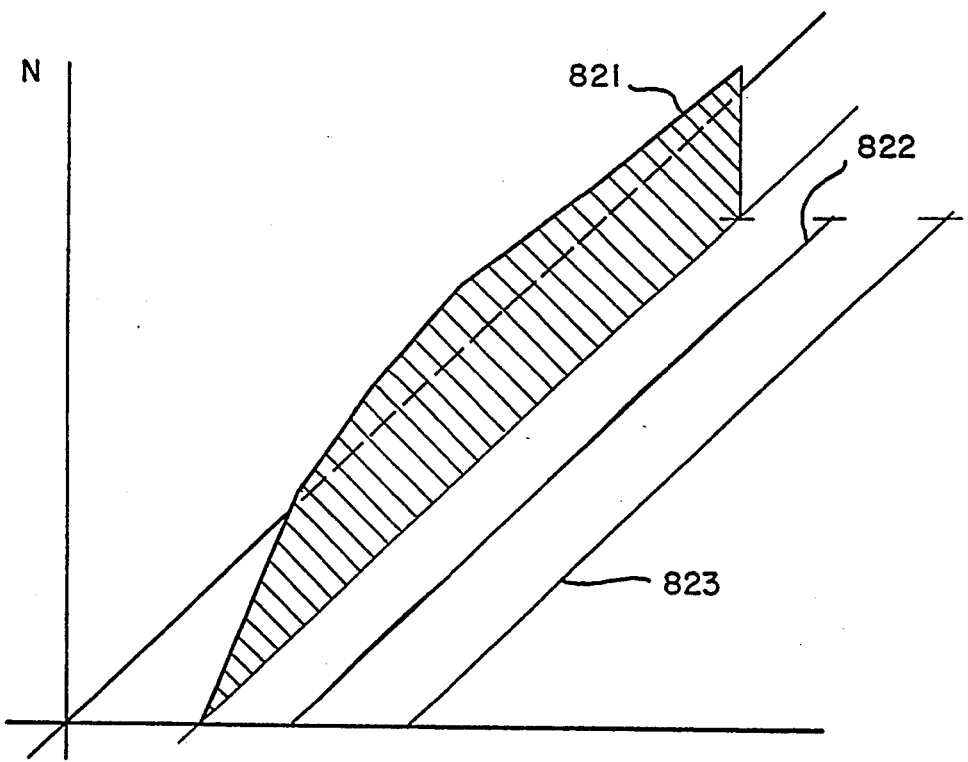
FIG. 16 is a series of graphs depicted in three dimensions (in a rectangular mode for the "x" and "y" axes) showing the relative attractiveness or repellency for air, bay leaf oil or the cycloalkanol derivative-containing composition of Parent Application, Ser. No. 887,138 filed on May 22, 1992 now U.S. Pat. No. 5,228,233 for or against Aedes aegypti. The graphs are based on experiments run for a period of one hour with six intervals of 10 minutes each. The results are tabulated in Table I, supra.

In FIG. 16, clean air is shown to attract mosquitoes (as indicated by the graph indicated by reference numeral 821). The mixture of compounds having the structures:

and

is shown to repel mosquitoes as indicated by the graph indicated by reference numeral 823. Bay leaf oil is also indicated to repel mosquitoes as indicated by the graph indicated by reference numeral 822.

Figure 35:
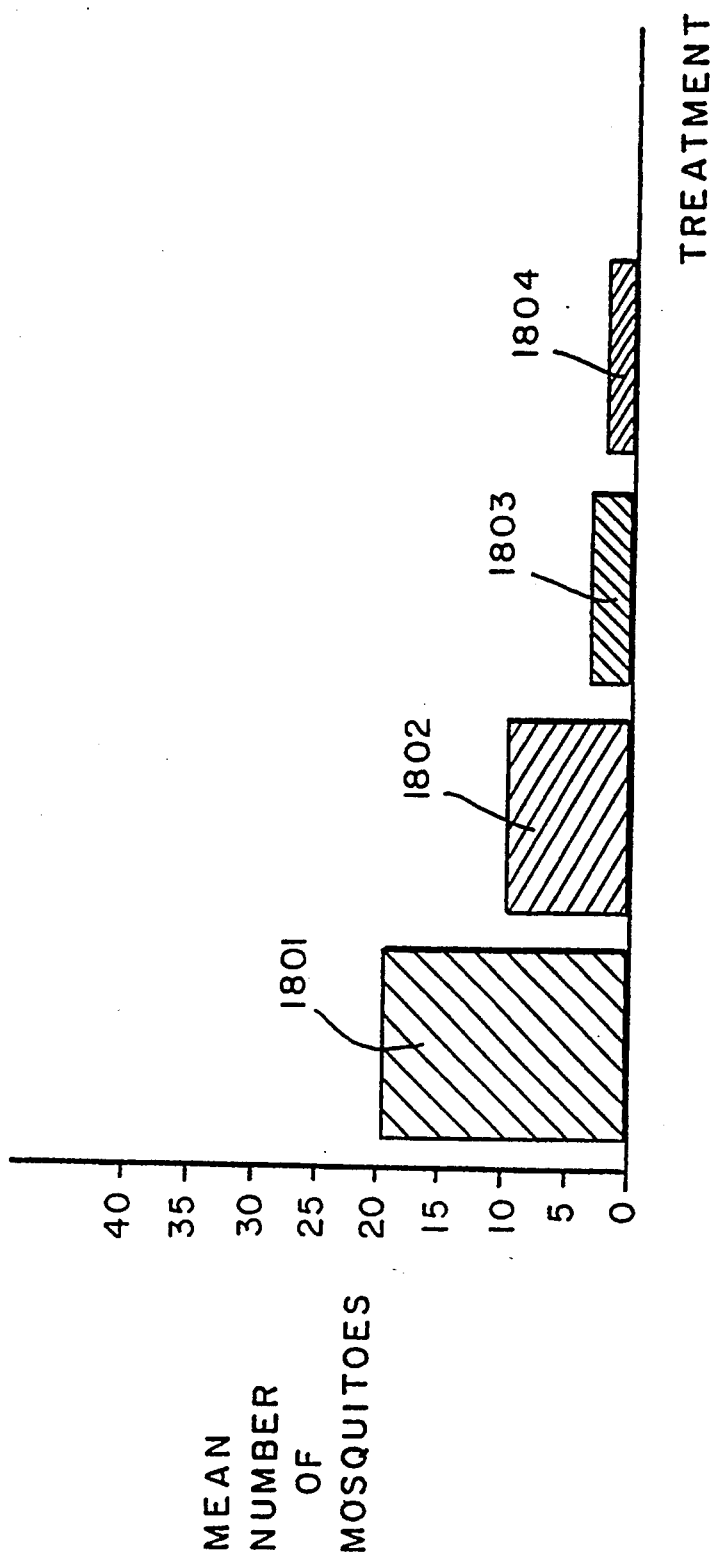
FIG. 35 is a bar graph showing a comparison of the field trial tests in the semiochemical field trap of FIG. 1 for blood feeding arthropods of our invention of repellence against mosquitoes and house flies, e.g., Musca domestica L.(Diptera:Muscidae), Aedes aegypti, Aedes albopictus, Anopheles spp., Coquillettidia perturbans, Culiseta spp., Culex spp., Psorophora spp., comparing in combination (with the use of pulsating infra-red light emitting diodes) air alone, the compound having the structure.

The bar graph of FIG. 35 shows the employment of the apparatus of FIG. 17 in testing the attractancy or repellency of various materials. It is shown that the mixture of compounds having the structures:

and

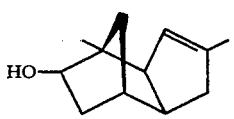

repels mosquitoes as shown by a low mean of bar graph 1804. It is shown that the compound having the structure:

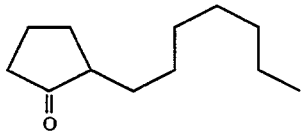

repels mosquitoes as shown by a low mean of bar graph 1803. It is shown that the compound having the structure:

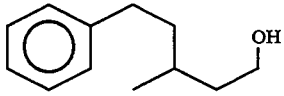

repels mosquitoes as shown by a low mean of bar graph 1802. On the other hand bar graph 1801 (for clean air) shows attractancy for mosquitoes.

The data shown in FIG. 35 is confirmed using a laboratory olfactometer of FIGS. 14 and 14A. This data is set forth in FIGS. 36A, 36B, 37A, 37B, 38A and 38B. In FIG. 36A *Aedes aegypti* is shown to be attracted by clean air (the graph indicated by reference numeral 2801 and is shown to be repelled by the compound having the structure:

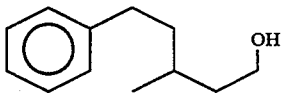

(shown by graph 2803) and by the mixture of compounds having the structures:

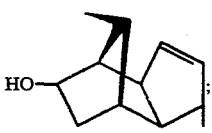

and

(shown by graph 2806.

In FIG. 36B, *Aedes aegypti* is shown to be attracted by clean air (the graph indicated by reference numeral 2811) and is shown to be repelled over a period of six hours by the compound having the structure:

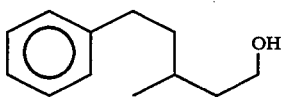

(shown by the graph indicated by reference numeral 2813) and the mixture of compounds having the structures:

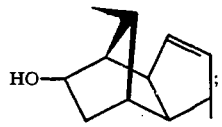

and

(shown by the graph indicated by reference numeral 2815).

In FIG. 37A, *Aedes aegypti* is shown to be attracted by clean air (the graph indicated by reference numeral 3801); is shown to be repelled by the compound having the structure:

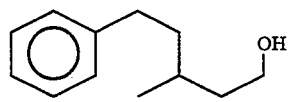

(the graph indicated by reference numeral 3805); is shown to be repelled by the compound having the structure:

(the graph indicated by reference numeral 3807) and is shown to be repelled by the mixture of compounds having the structures:

and

(the graph indicated by reference numeral 3803). In FIG. 37B, *Aedes aegypti* is shown to be attracted by clean air (the graph indicated by reference numeral 3811); and is shown to be repelled by the mixture of compounds having the structures:

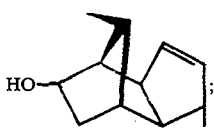

and

(the graph indicated by reference numeral 3813); is shown to be repelled by the compound having the structure:

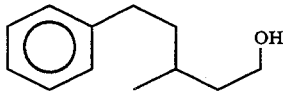

(the graph indicated by reference numeral 3815) and is shown to be repelled by the compound having the structure:

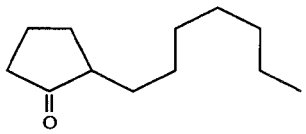

(the graph indicated by reference numeral 3817). In FIG. 38A, *Aedes aegypti* is shown to be attracted by clean air (the graph indicated by reference numeral 4813) and is shown to be repelled by the compound having the structure:

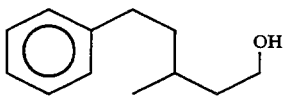

(the graph indicated by reference numeral 4811). In FIG. 38B, *Aedes aegypti* is shown to be attracted by clean air (the graph indicated by reference numeral 4803) and is shown to be repelled by the compound having the structure:

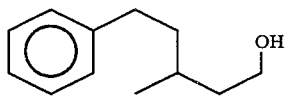

(the graph indicated by reference numeral 4801).

The olfactometer illustrated in FIG. 14 and the olfactometer section illustrated in FIG. 14A are described in U.S. Pat. No. 4,748,860 issued on Jun. 7, 1988 the specification for which is incorporated herein by reference.

In FIG. 14, air source 734 feeds air through line 735 through air distributors 736, 736a, et seq. onto base plate 717 containing insect landing sites 710, 710a, et seq. The base plate 717 is separated from the spacer plate 729 for the air lines 736, 736a, et seq. whereby the air lines 736, 736a, et seq. are held in place at positions 731 and 731a. Air exists through line 733a using exhaust fan 733. The olfactometer is assisted with computer apparatus shown in schematic form and block flow diagram form using reference numerals 720, 721, 723, 724 and 739. Dampers 711a, 711b, et seq. hold base plate 717 in place horizontally. When an insect lands on sensor landing site 710, 710a et seq. the landing is recorded electrically through a sensor shown in magnified form in FIG. 14A. The sensor landing site includes a transducer 713 and causes an electrical impulse to proceed through wire 718 and then through wire 719 to a multi-channel A-D converter 723 (using electric power source 739) which is associated with program tape storage 724, printer 720 and digital computer which is associated with modem and main frame 721. Reference numeral 722 shows a "Faraday" cage completing the olfactometer circuit. The electrical impulse thus effects a recording of data as set forth in FIGS. 15 and 16.

FIG. 14A is a detailed section showing one specific landing site 710a of FIG. 14 on which the insect lands if attracted by one of the alkyl cyclopentanone or phenylalkanol derivative-containing compositions of our invention taken alone or in admixture with the cycloalkanol derivative-containing composition containing compounds having the structures:

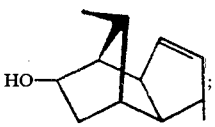

and

or does not land if repelled by, for example, one of the alkyl cyclopentanone or phenylalkanol derivative-containing compositions of our invention having the structures:

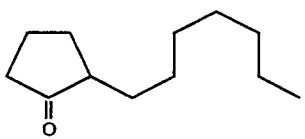

or

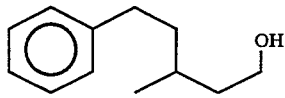

taken alone or in admixture with the mixture of compounds having the structures:

and

which is also located at specific landing sites. At other landing sites nothing is located (and these are the "control" landing sites). At other sites, a second repellent can be located, e.g., the bay leaf oil or an attractant can be located. The olfactometer includes a base 781 on which the damper 711a, 711b, et seq. are located, namely base 781. Base plate 717 is preferably covered with a film such as SARAN WRAP ® 725 so that any insects that are attracted to the landing sites are not distracted to any other areas on base plate 717.

A preferred embodiment of our invention involves the use of articles set forth in FIGS. 25–34 which comprises an ellipsoidally-shaped detergent tablet 830. containing a solid plastic core 832 which can be fabricated from, for example, polyethylene, polypropylene, nylon or any polymer capable of having therein microvoids from which an insect repelling substance, e.g., the compound having the structure:

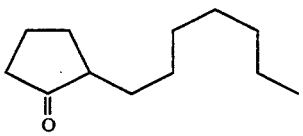

the compound having the structure:

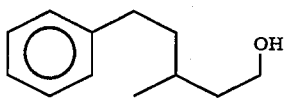

will be controllably transported from the plastic core into and through the soap cake over a reasonable period of time during the use of the soap cake (as when the user washes skin with said soap cake). Such polymers can be microporous polymers such as those described in U.S. Pat. No. 4,247,498 issued on Jan. 27, 1981, the specification for which is incorporated herein by reference. Surrounding the central plastic core containing insect repellent 832 is detergent 830' which is in the solid phase at ambient conditions, e.g., room temperature and atmospheric pressure. Examples of workable detergents 830' are "elastic" detergents such as those described in U.S. Pat. No. 4,181,632 issued on Jan. 1, 1980, the disclosure of which is incorporated herein by reference, or "transparent" soaps such as those set forth in U.S. Pat. No. 4,165,293 issued on Aug. 21, 1979, the disclosure of which is incorporated herein by reference. Other examples of the detergent 830' useful in our invention are those set forth as "variegated soaps" in Canadian Letters Patent No. 1,101,165 issued on May 19, 1981, the disclosure of which is incorporated herein by reference.

On use of the soap tablet 830 or detergent bar, the insect repellent agent, e.g., the compound having the structure:

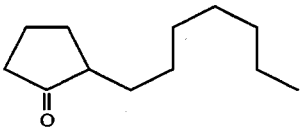

or the compound having the structure:

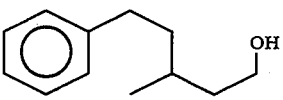

originally located in the plastic core 832 is transported at a steady state from core 832 through core surface 831 through the detergent 830' and finally through the surface of the detergent bar at, for example, 833, 834, 835 and 836.

The detergent bar or tablet 830 of our invention may be of any geometric shape, for example, a rectangular parallelpiped tablet as shown in FIGS. 29, 30 and 31 containing solid plastic core 839. the insect repellent located in solid plastic core 839 on use of the detergent bar passes through at steady state, surface 837 of FIG. 31, detergent 838 and finally the surface of the detergent 838 at, for example, locations 841, 842, 843 and 844. The environment surrounding the detergent bar on use thereof is then treated with insect repellent, e.g., the compound having the structure:

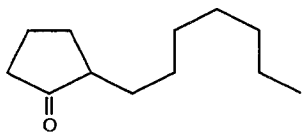

or the compound having the structure:

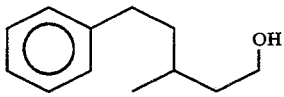

at locations 841, 842, 843 and 844, for example.

As shown in FIGS. 32, 33 and 34, the plastic core of the detergent tablet 830 may have a single finite void at its center 851 (of FIGS. 33 and 34) in which the insect repellent agent and optionally the aromatizing agent is contained. The plastic core then is a shell 848 having outer surface 852 (shown in FIGS. 33 and 34). The insect repellent agent (and optionally the aromatizing agent) contained in the void in the plastic core permeates through shell 848, past surface 852 at a steady state, through the detergent 847 into the environment at, for example, 856, 857, 858 and 859.

In addition to the insect repellent contained in the core, e.g., core 839 or core void, the core can also contain other materials for therapeutic use, for example, bacteriostats, deodorizing agents and the like which are compatible with insect repellents such as the compound having the structure:

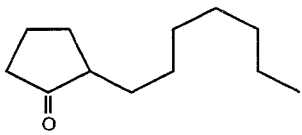

or the compound having the structure:

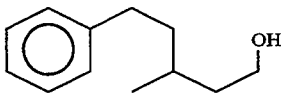

or mixtures of said compounds with the mixture of compounds having the structures:

and

-continued

of our invention. In the alternative, the plastic core of the detergent tablet of FIGS. 32, 33 and 34 may have an empty single finite void at its center 851 with the insect repellent contained in the shell 848.

At the end of the use of the detergent tablet (e.g., using it in a washing machine, for example) the hollow core or the solid core can be used as an insect repelling and aroma imparting or air freshener household article. In addition, depending on the ratio of the volume of the void 851, to the solid part of the detergent tablet of FIGS. 32, 33 and 34, the detergent tablet of FIGS. 32, 33 and 34 can be so fabricated that it will float on the surface of the liquid in which it is being used and this physical attribute has certain obvious advantages.

What is claimed is:

1. A method of repelling at least one of the insect species:
    (a) *Musca domestica* L. (Diptera:Muscidae);
    (b) *Aedes aegypti;*
    (c) *Aedes albopictus;*
    (d) Anopheles spp.
    (e) *Coquillettidia perturbans;*
    (f) Culiseta spp.;
    (g) Culex spp.;
    (h) Psorophora spp.;
    (i) Culicoides spp.; and/or
    (j) Lutzomyia spp.

for a finite period of time from a three dimensional space comprising the step of exposing said three dimensional space to a:
    (a) *Musca domestica* L. (Diptera:Muscidae);
    (b) *Aedes aegypti;*
    (c) *Aedes albopictus;*
    (d) Anopheles spp.
    (e) *Coquillettidia perturbans;*
    (f) Culiseta spp.;
    (g) Culex spp.;
    (h) Psorophora spp.;
    (i) Culicoides spp.; and/or
    (j) Lutzomyia spp.

repelling concentration and quantity of an insect repellent composition of matter which comprises an alkylcyclopentanone and phenyl alkanol derivative-containing composition of chemicals selected from the group consisting of:

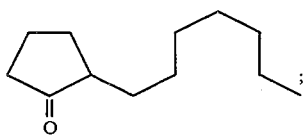 (i)

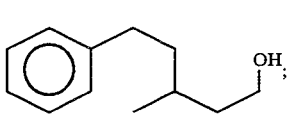 (ii)

(iii) a mixture of the compound having the structure:

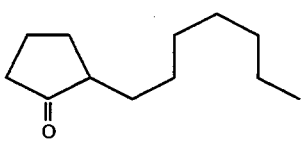

with a cycloalkanol derivative-containing composition of chemicals having the structures:

and

and (iv) a mixture of the compound having the structure:

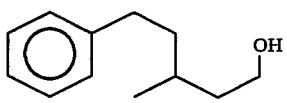

with a cycloalkanol derivative-containing composition of chemicals having the structures:

and

2. The method of claim 1 wherein the cycloalkanol derivative-containing composition is produced by the process of reacting an alkanoic acid with a mixture of chemicals having the structures:

and

in the presence of a protonic acid catalyst or a Lewis acid catalyst and then subjecting the resulting mixture to hydrolysis.

3. The method of claim 1 which is a method of repelling mosquitoes for a finite period of time from a three dimensional space comprising the step of exposing said three dimensional space to a mosquito repelling concentration and quantity of an insect repellent composition of matter which comprises an alkycyclopentanone or phenyl alkanol derivative-containing composition selected from the group consisting of:

(i)

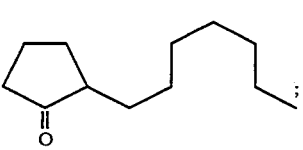

(ii)

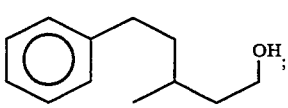

(iii) a mixture of the compound having the structure:

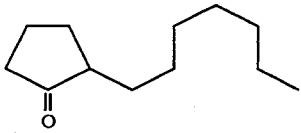

with a mixture of the compounds having the structures:

-continued and

and (iv) a mixture of the compound having the structure:

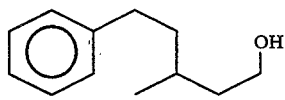

with a mixture of the compounds having the structures:

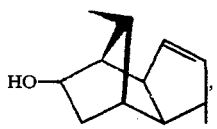

and

4. The method of claim 1 which is a method of repelling the insect species *Musca domestica* L. (Diptera:-Muscidae) for a finite period of time from a three dimensional space comprising the step of exposing said three dimensional space to a *Musca domestica* L. (Diptera:-Muscidae) repelling concentration and quantity of an insect repellent composition of matter which is an alkylcyclopentanone or phenylalkanol derivative-containing composition selected from the group consisting of:

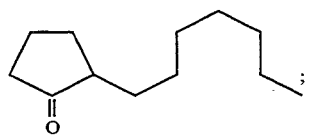 (i)

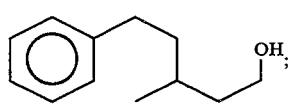 (ii)

(iii) a mixture of the compound having the structure:

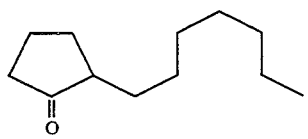

with a mixture of the compounds having the structures:

and

and (iv) a mixture of the compound having the structure:

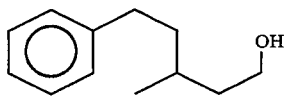

with a mixture of the compounds having the structures:

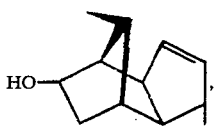

and

5. A process for repelling blood feeding arthropods from a person consisting of the steps of:
   (a) fabricating an insect repelling soap comprising a soap base and in intimate contact therewith an alkylcyclopentanone or phenylalkanol derivative-containing composition selected from the group consisting of:

(i) 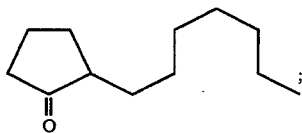

(ii) 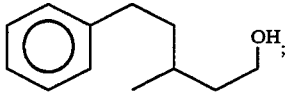

(iii) a mixture of the compound having the structure:

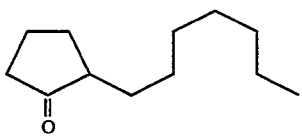

with a mixture of cycloalkanol derivatives having the structures:

and

and
(iv) a mixture of the compound having the structure:

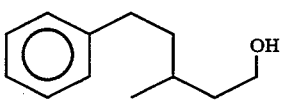

with a mixture of cycloalkanol derivatives having the structure:

and

and (b) applying an effective amount of the thus fabricated soap to said person.

6. The method of claim 3 wherein the insect repelling composition of matter is an insect repelling perfume composition comprising a perfume base and intimately admixed therewith an insect repelling amount of an alkylcyclopentanone or phenylalkanol derivative-containing composition selected from the group consisting of:

(i) 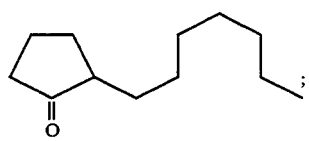

(ii) 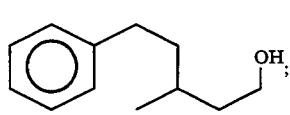

(iii) a mixture of the compound having the structure:

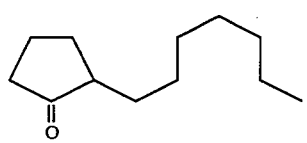

with a mixture of cycloalkanol derivatives having the structures:

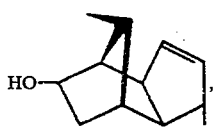

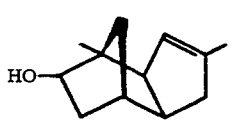

and

-continued
and
(iv) a mixture of the compound having the structure:
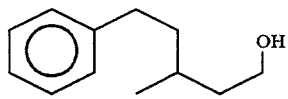
with a mixture of cycloalkanol derivatives having the structures:
,
and
.
* * * * *